(12) United States Patent
Nagamoto

(10) Patent No.: US 7,037,338 B2
(45) Date of Patent: May 2, 2006

(54) INTRAOCULAR RING ASSEMBLY AND ARTIFICIAL LENS KIT

(76) Inventor: Toshiyuki Nagamoto, 29-23, Nozawa 2-chome, Setagaya-ku, Tokyo (JP)

( * ) Notice: Subject to any disclaimer, the term of this patent is extended or adjusted under 35 U.S.C. 154(b) by 155 days.

(21) Appl. No.: 10/295,856

(22) Filed: Nov. 18, 2002

(65) Prior Publication Data
US 2003/0114927 A1 Jun. 19, 2003

(30) Foreign Application Priority Data
Dec. 14, 2001 (JP) .............................. 2001-380870

(51) Int. Cl.
*A61F 2/16* (2006.01)
(52) U.S. Cl. ..................... 623/6.37; 623/4.1; 623/6.4; 623/6.39
(58) Field of Classification Search .............. 623/4.1, 623/6.11, 6.37–6.43, 6.47
See application file for complete search history.

(56) References Cited

U.S. PATENT DOCUMENTS

| | | | | |
|---|---|---|---|---|
| 4,842,601 A | * | 6/1989 | Smith | 623/6.34 |
| 5,326,347 A | * | 7/1994 | Cumming | 623/6.38 |
| 5,522,891 A | * | 6/1996 | Klaas | 623/6.37 |
| 6,013,101 A | * | 1/2000 | Israel | 623/6.43 |
| 6,443,985 B1 | * | 9/2002 | Woods | 623/6.46 |
| 6,464,725 B1 | * | 10/2002 | Skotton | 623/6.34 |
| 6,488,708 B1 | * | 12/2002 | Sarfarazi | 623/6.34 |
| 6,761,737 B1 | * | 7/2004 | Zadno-Azizi et al. | 623/6.37 |
| 2003/0130732 A1 | * | 7/2003 | Sarfarazi | 623/6.13 |

FOREIGN PATENT DOCUMENTS

JP        02011134 A    *  1/1990

* cited by examiner

*Primary Examiner*—David H. Willse
*Assistant Examiner*—Javier G. Blanco
(74) *Attorney, Agent, or Firm*—Snider & Associates; Ronald R. Snider

(57) ABSTRACT

An intraocular ring assembly and an artificial lens kit, both of which are usable for implantation in a lens capsule or capsular bag of natural eye. The intraocular ring assembly includes a first ring element having recessions therein, a second ring element, and a biasing element provided between the first and second ring elements. The artificial lens kit comprises such intraocular ring assembly and an intraocular lens to be movably supported in the recessions of the ring assembly in a coaxial relation therewith. A guide element may be provided to assist in rectilinear coaxial movement of the first and second ring elements.

5 Claims, 23 Drawing Sheets

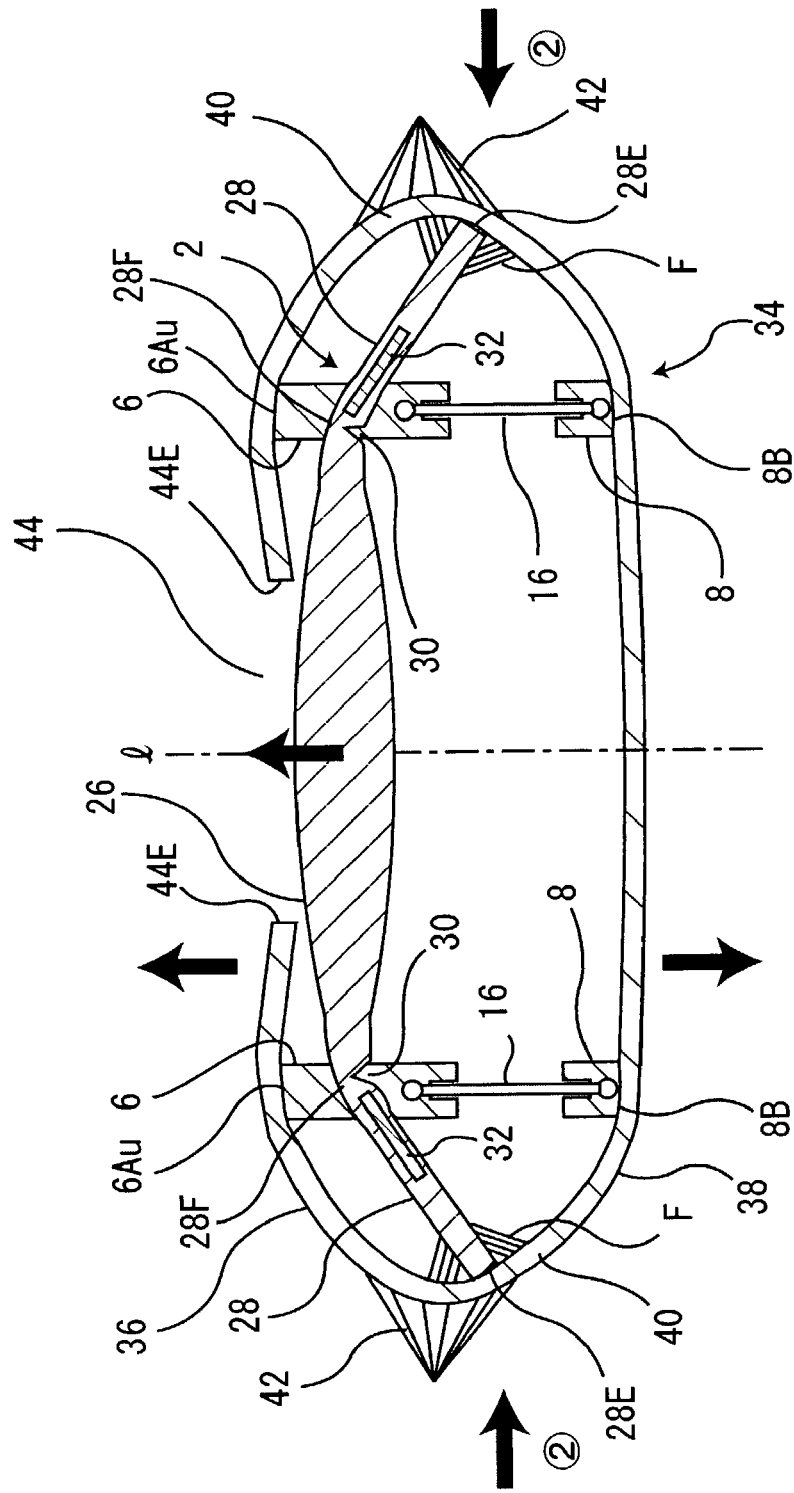

INTRAOCULAR RING ASSEMBLY AND ARTIFICIAL LENS KIT

BACKGROUND OF THE INVENTION

1. Field of the Invention

The present invention relates to an accommodating intraocular lens to be implanted in a lens capsule (or a capsular bag) of human or natural eye in a surgical procedure subsequent to extracapsular cataract extraction. In particular, the invention is directed to a novel intraocular ring assembly and a novel artificial lens kit for implantation in the lens capsule or capsular bag, which are designed to enable the eye to have an optimal accommodation to gain near and distant visions.

2. Description of Prior Art

A human eye has a crystalline lens which is endowed with accommodation, i.e. a natural focal function in the lens to adjust its focus on an object being moved from a far distance to a nearby distance, or vice versa, so that a human being with the eyes can keep a clear vision for the moving object.

It is generally believed that the accommodation of human eye is based on the following actions: When the eye gazes at an object located at a far distance, a crystalline lens in the eye, which substantially serves as an artificial optical lens, is kept in a flattened state. Now, when the eye changes its gazing from the object at a far distance to a new object located at a nearby distance, a circular ciliary muscle (a circular muscle of ciliary body (at 50 in FIG. 21)) circumscribing the crystalline lens is contracted to cause relaxation of zonule of Zinn (see the designation 42 in FIG. 21), because of the lens being connected via the zonule (plural thin fibrous tissues) with a ciliary body (at 50 in FIG. 21). Such relaxation of zonule allows the crystalline lens to become inflated into a spherical shape, increasing its thickness, due to the inherent elastic expansive property of the lens, whereby the refractive power of the lens is increased so as to properly adjust a focus on the object at near distance, thus attaining a clear vision thereof.

By contrast, when the eye changes its gazing from the nearby object to a far distant object, the actions are reversal: the circular ciliary muscle mentioned above is then relaxed to cause traction of the crystalline lens via the zonule, thereby stretching the crystalline lens outwardly, with the result that the lens is transformed into a flattened shape from the spherical shape, thus decreasing the refractive power of the lens so as to properly adjust focus on the far distant object.

The crystalline lens is normally transparent, but, for some reasons or other, the lens itself is subjected to opacification. In that case, a light entering the eye is scattered by the opacified crystalline lens before reaching a retina, and therefore, a precise image can hardly be formed at the retina or fundus, which results in a misted or dim vision. In most cases, this symptom is what is generally known as "cataract". The nature of the cataract varies according to different causes, such as an age-related cataract, a congenital cataract, a diabetic cataract, a traumatic cataract, and a glass-blower's cataract due to an occupational disease caused by exposure to infrared rays. Recent years witness an increased number of cataract patients.

A brief explanation will be made as to the crystalline lens. Crystalline lens is in the form of a biconvex lens and has a transparent outer thin capsular membrane with an elastic property, which covers the entirety of an inner lens matrix. Such capsular outer membrane is what is referred to as "lens capsule". Ophthalmologically stated, the lens capsule is divided into a forward portion facing to a cornea (see the designation 52 in FIG. 21); i.e. what is referred to as "anterior capsule", and a rearward portion facing to a vitreous (see the designation 53 in FIG. 21); i.e. what is referred to as "posterior capsule".

The boundary between those anterior and posterior capsules is the so-called "equator" which expends along the outer circumference of the lens capsule. Integrally fixed to the periphery of the lens capsule substantially corresponding to the equator is the zonule which connect the crystalline lens and the ciliary body.

Typical treatment for the foregoing crystalline lens disease, or the cataract, includes an intraocular lens implantation to replace an opacified natural lens. This sort of procedure normally entails the steps of making an incision to the anterior capsule of the lens to form a circular opening therein, then extracting an inner matrix from the lens capsule via such circular opening to leave an empty capsule or the so-called capsular bag, and thereafter, implanting an intraocular lens in that capsular bag.

Conventional intraocular lenses, however, do not provide a sufficient accommodation since they are incapable of increasing and decreasing the thickness of the lens itself, and do not insure a precise forward and backward movement of the lens in the direction anteriorly and posteriorly of eye. Yet, almost all of the conventional intraocular lenses are not designed to gain an optimum focus on near and distant objects, and, in most cases, they still rely on a fixed focus, resulting in a wearer of the intraocular lenses requiring eyeglasses. As a consequence thereof, it can be mentioned that the conventional intraocular lenses can not work with ciliary body and zonule to a satisfactory degree, and therefore, have not yet achieved an optimum focus on every object located at near or far distance, raising the problem that the lens wearer can not have a satisfactory clear vision for various objects at all ranges of distances and will encounter any unexpected inconvenience and trouble postoperatively.

SUMMARY OF THE INVENTION

With the above-stated shortcomings in view, it is a purpose of the present invention to provide an intraocular ring assembly that is of such a structure that allows its ideal implantation in a lens capsule or capsular bag of natural eye, while achieving a high sensitivity to changes in shape of the lens capsule due to contraction and relaxation of the ciliary body via the zonule, and also preventing after-cataract problem.

In order to attain such purpose, the intraocular ring assembly in accordance with the present invention is basically comprised of:

a first ring element having a center;
a second ring element having a center;
at least two recessions defined in said first ring element; and
a biasing means provided between said first ring element and said second ring element,
wherein the first and second ring elements are resiliently supported by the biasing means such that the center of the first ring element is in a coaxial relation with the center of the second ring element, and wherein the biasing means resiliently urges the first and second ring elements in a direction opposite to each other.

It is another purpose of the present invention to provide an artificial lens kit which can be effectively used for implantation in a lens capsule or capsular bag of natural eye in order to realize a proper accommodation of the eye with a high sensitivity to changes in shape of the lens capsule due to contraction and relaxation of the ciliary body via the zonule, while preventing after-cataract problem.

For that purpose, the artificial lens kit in accordance with the present invention is basically comprised of:

an intraocular lens having an optic portion and a haptic means provided on a peripheral end of said optic portion, the haptic means being adapted to contact an inner surface of a lens capsule corresponding to an equator of the lens capsule; and an intraocular ring assembly in which the intraocular lens is supported in a coaxial relation therewith, which intraocular ring assembly includes:

a first ring element having a center and a support means for supporting the haptic means of the intraocular lens therein, the first ring element having one side adapted to be contacted with the anterior capsule and another side opposite to that one side;

a second ring element having a center and one side adapted to be contacted with the posterior capsule and another side opposite to that one side; and a biasing means provided between the first ring element and the second ring element;

wherein the biasing means resiliently urges the first ring element in a direction to the anterior capsule, while resiliently urging the second ring element in a direction to the posterior capsule.

In a first aspect of the invention, the support means may comprise at least two support recessions defined in the first ring means, and each of the at least two haptic portions may include a base area connected with the peripheral end of optic portion and is so formed as to be movably supported in each of the at least two support recessions at a point adjacent to the base area thereof.

In a second aspect of the invention, each of the at least two haptic portions may include a bendable means defined adjacent to the base area thereof, the bendable means being adapted to render each of the at least two haptic portions bendable at that base area in a vertical direction relative to the optic portion.

In a third aspect of the invention, the bendable means may comprise a cutout formed in one side of each of the at least two haptic portions in proximity to the base area.

In a fourth aspect of the invention, a first securing means may be provided in the first ring means, while a second securing means be provided in the second ring means, and the biasing means be secured by and between the first and second securing means.

In a fifth aspect of the invention, the biasing means may comprise at least two elastic elements each having a generally figure-of-eight or circular configuration.

In a sixth aspect of the invention, each of the first and second securing means may comprise at least two grooves and at least one securing cavity formed in each of the at least two grooves, and further may include at least one anchor portion formed in the biasing means, so that the at least one anchor portion is securely engaged in the at least one securing cavity and the biasing means is partway fitted in the groove.

In an eighth aspect of the invention, a guide means may be provided between the first and second ring elements, the guide means being adapted to assist in a rectilinear coaxial movement of the first and second ring elements.

In a ninth aspect of the invention, the biasing means may be integrally and directly connected between the first and second ring elements.

In a tenth aspect of the invention, a fibronectin or fibronectin-like substance may be included, which is applied to a part of or a substantially whole of said at least two haptic portions of said intraocular lens element.

Other various features and advantages of the present invention will become apparent from reading of the descriptions hereinafter, with reference to the annexed drawings.

BRIEF DESCRIPTION OF THE DRAWINGS

FIG. 23 is a diagram which explanatorily shows the state where the capsular bag becomes swollen into spherical form via the assembled unit of artificial lens kit when the capsular bag is released from the stretched state by relaxation of zonule.

DETAILED DESCRIPTION OF PREFERRED EMBODIMENTS OF THE INVENTION

Figure 1:
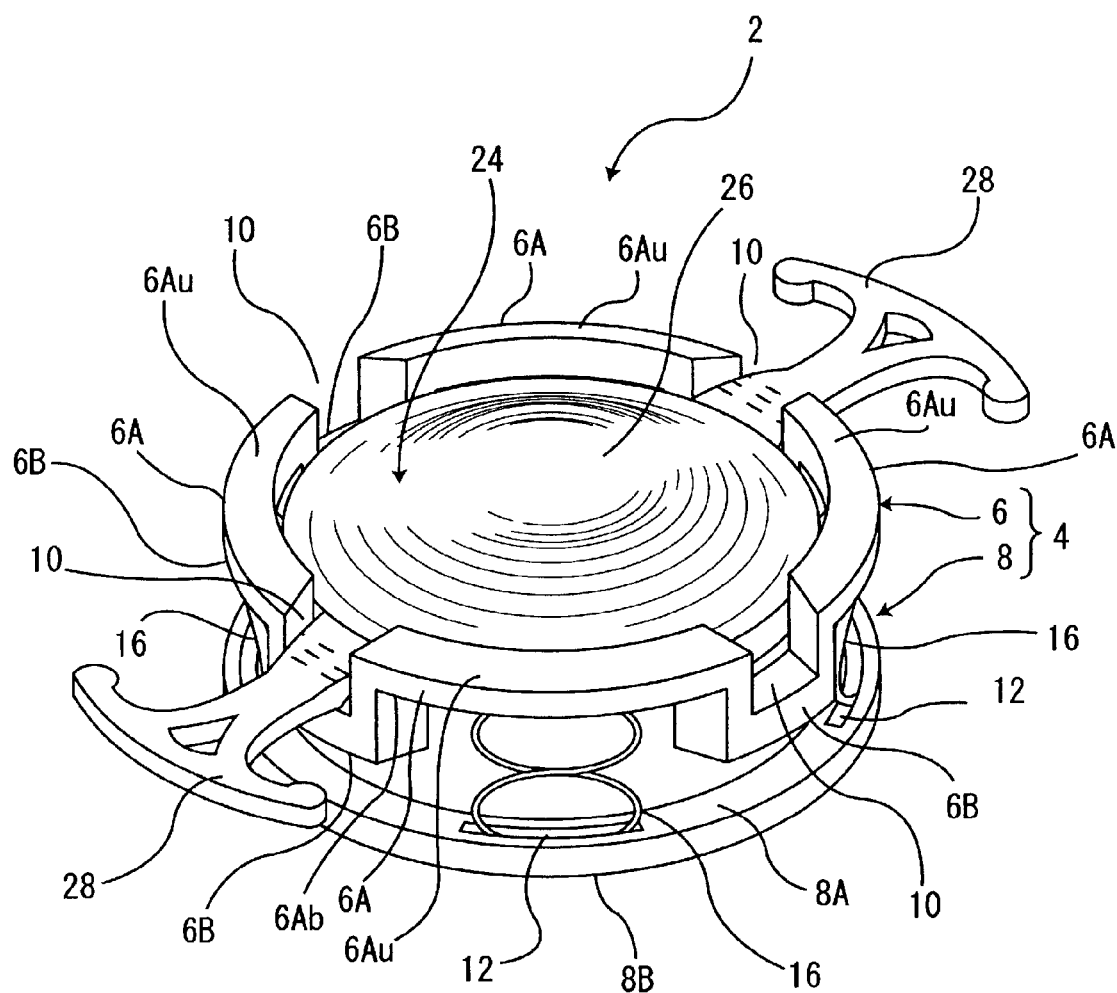
FIG. 1 is a schematic perspective view showing one exemplary mode of artificial lens kit in accordance with the present invention.

Referring to FIGS. 1 through 23, reference numeral 2 generally represents an artificial lens kit that can be used for implantation in a lens capsule or a capsular bag of a natural or human's eye within the gist and scopes of the present invention.

Figure 2:
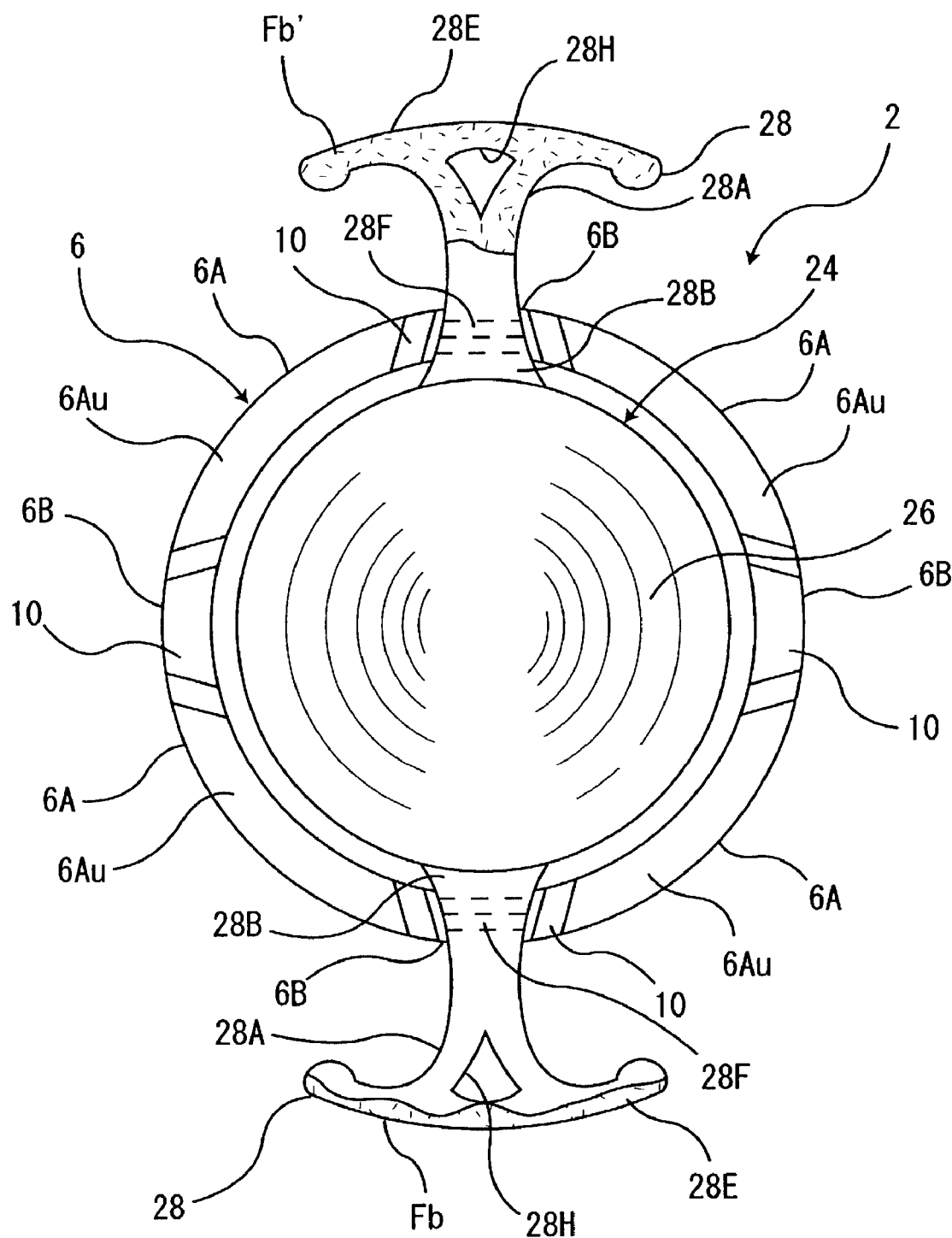
FIG. 2 is a front view of the artificial lens kit.
Figure 3:
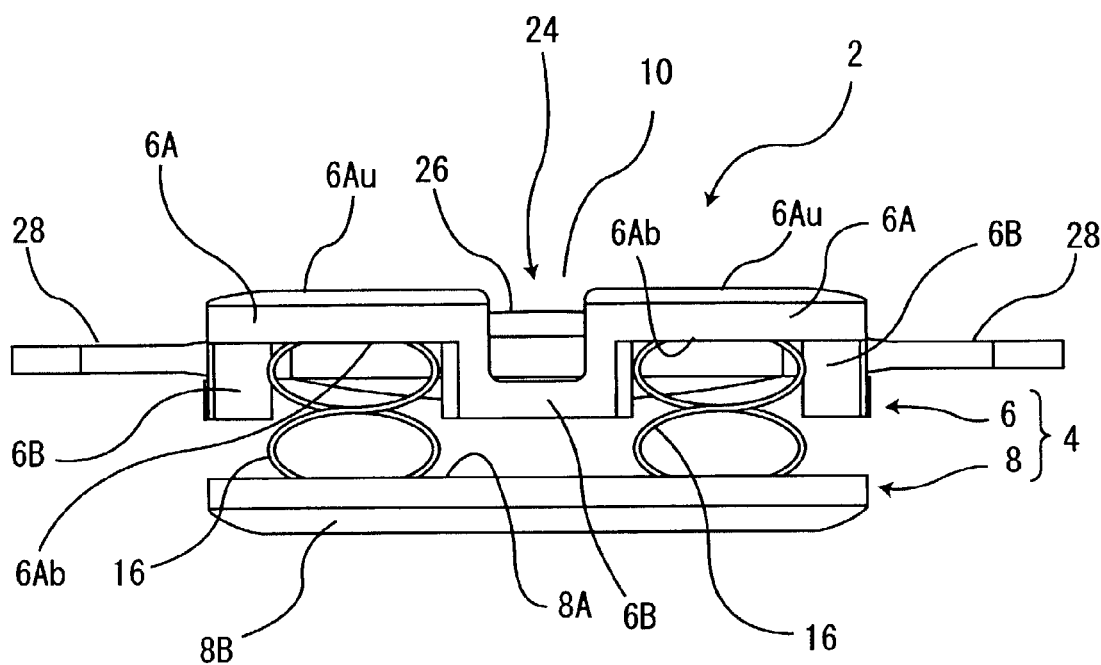
FIG. 3 is a side elevational view of the artificial lens kit.

In particular, FIGS. 1 to 3 are illustrative of one preferred mode of the artificial lens kit in the present invention, which is presented for exemplary purpose only, and therefore, the invention is not limited to the shown embodiments.

The artificial lens kit 2 is basically comprised of an intraocular lens 24 and an intraocular ring assembly 4 in which the lens 24 is movably supported. As will be described later, this artificial lens kit 2 is to be implanted within a lens capsule of natural crystalline lens, or in most cases, it is to be implanted within a capsular bag 34 (see FIG. 21) which is an empty lens capsule from which an inner lens matrix has been extracted from a natural lens capsule by extracapsular cataract extraction, for instance. Of course, it is essential that a center of the intraocular lens 24 and a center of the ring assembly 4 should be in a coaxial relation with each other, and that their central axes be coaxial with an optical axis 1 of eye ball E when placing the lens unit 2 in the capsular bag 34, as can be seen from FIG. 21. Hereinafter, description will be made in the case where the kit 2 is to be assembled and placed or implanted in the capsular bag 34.

FIGS. 7 to 11(B) show one exemplary mode of the intraocular ring assembly 4. In this mode, the ring assembly 4 is composed of an anterior ring element 6, a posterior ring element 8, and a plurality of elastic biasing elements 16 provided between the anterior and posterior ring elements 6, 8. It is should be understood, referring to FIG. 21, that the anterior ring element 6 is to be disposed at a side facing to the anterior capsule 36 of natural crystalline lens or capsular bag 34, whereas the posterior ring element 8 is to be disposed at a side facing to the posterior capsule 38 of the crystalline lens or capsular bag 34. Those two ring elements 6, 8 are assembled together via the elastic biasing elements 16 in a mutually coaxial relation. Again, essentially, the centers (or central axes) of the two ring elements 6, 8 be in a coaxial relation with the optical axis 1 when placing the lens kit 2 in the capsular bag 34.

Both anterior and posterior ring elements 6, 8 are depicted in the figures to assume a perfect circular configuration, but, in general, they may be formed in any desired fashion analogous to a circle for optimum implantation in the capsular bag 34. Both two ring elements 6 and 8, a principal part of the intraocular ring assembly 4, may preferably be formed from a soft elastic material, such as acrylic or silicon, that can be easily and resiliently deformed. Needless to mention, an optic portion 26 of the intraocular lens 24, which is to be incorporated in the intraocular ring assembly 4, may be formed from the foregoing soft elastic material, as well. This is because, in most cases, the recent intraocular lens implantation procedure involves folding or rolling an elastic intraocular lens into a small piece which is then inserted into a capsular bag so that it resiliently unfolds into an original lens shape therein, and, for that purpose, both intraocular lens 24 and intraocular ring assembly 4 may preferably be formed from the soft elastic material. However, where no soft elastic material is used, the corresponding portions of intraocular ring assembly 4 may be formed in any desired structure or shape (not shown) that permits it to be folded or rolled and then recovered into its original shape.

Preferred dimensions of the anterior and posterior ring element 6, 8 are commonly such that the outer diameters of those two ring elements 6, 8 may be set in the ranges of from 7.0 mm to 8.0 mm, whereas the inner diameters of the same (6, 8) be set in the ranges of from 6.0 mm to 7.0 mm, and the height-wise thickness of each ring element 6 or 8, as viewed from the side elevation of FIG. 3 for instance, may be in the ranges of from 1.5 mm to 2.5 mm. These parameters are found effective in designing the two ring elements 6, 8 for implantation in an ordinary size of crystalline lens or capsular bag 34. Of course, this is not limitative and the dimensions of the ring elements 6, 8 may be set as desired insofar as they serve the purposes of the present invention.

In the illustrated embodiment, the anterior ring element 6 is formed by four first sectorial ring portions 6A and four second sectorial ring portions 6B in such a manner that those first and second sectorial ring portions 6A, 6B are disposed equidistant in an alternately offset way. Otherwise stated, each second sectorial ring portion 6B is recessed vertically from the adjoining two first sectorial ring portions 6A that extends horizontally along the circumference of anterior ring element 6, thereby, in the aggregate, defining four generally "U" shaped ring portions (i.e. 6B) protruding equidistantly from the respective four first sectorial ring portions 6A in a vertical direction along the central axis of the ring element 6 as viewed from the figures. Hereinafter, the second sectorial ring portion 6B will be referred to as "generally U-shaped ring portion 6B" for a better understanding of the present invention.

Each first sectorial ring portion 6A has a first end surface 6Au and a second end surface 6Ab opposite thereto. The first end surface 6Au slopes upwardly in a gradual way (at a relatively small angle of inclination) as it proceeds toward the center (or central axis) of the anterior ring element 6 (i.e. in a direction from the outer arcuate wall thereof to the inner arcuate wall thereof), as can be seen from FIGS. 1 and 3. This end surface 6Au may be formed flat, but, such sloped formation thereof is recommended to allow the ring element 6 to be smoothly placed within the capsular bag 34 in a moderate and intimate contact with and along the generally concave inner surfaces of the capsular bag 34 (which serves to prevent damage to that capsular bag 34 per se).

Figure 8:
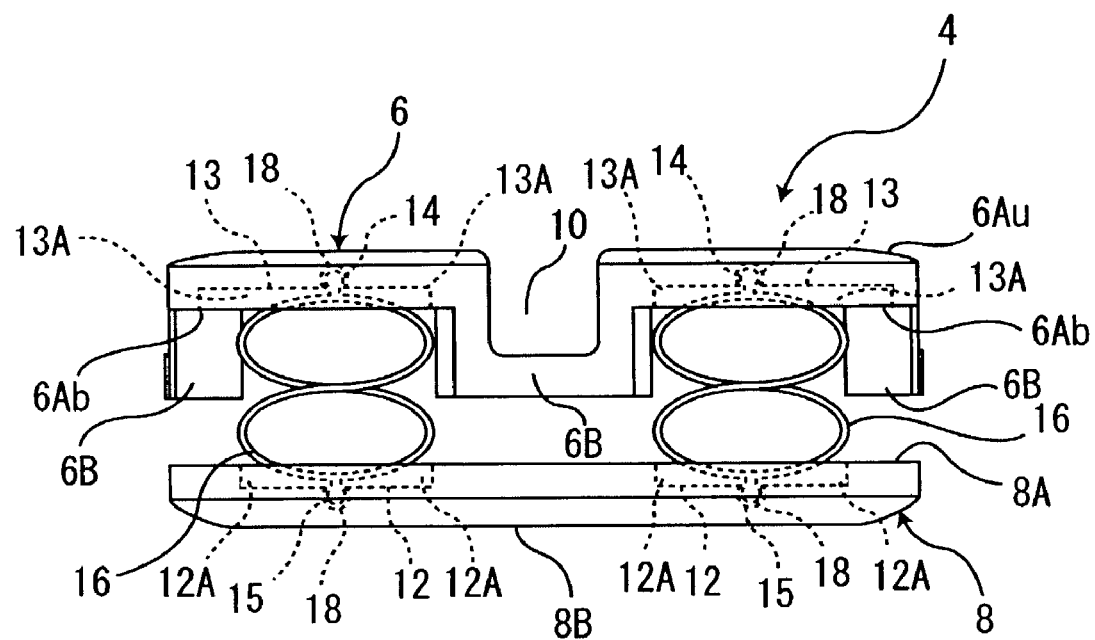
FIG. 8 is a side elevational view of the intraocular ring assembly shown in the FIG. 7.
Figure 9:
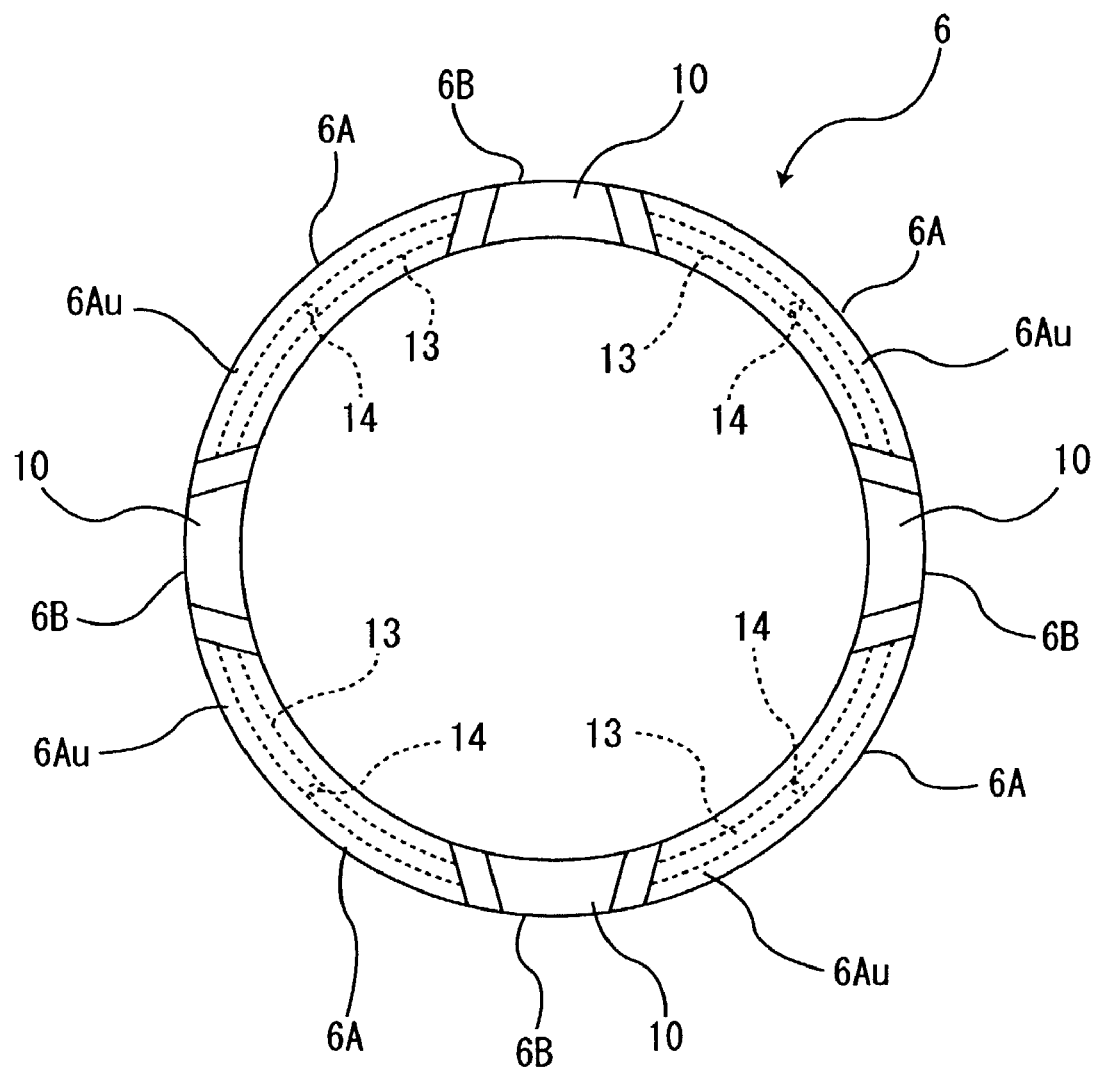
FIG. 9 is a front view of the intraocular ring assembly.
Figure 10:
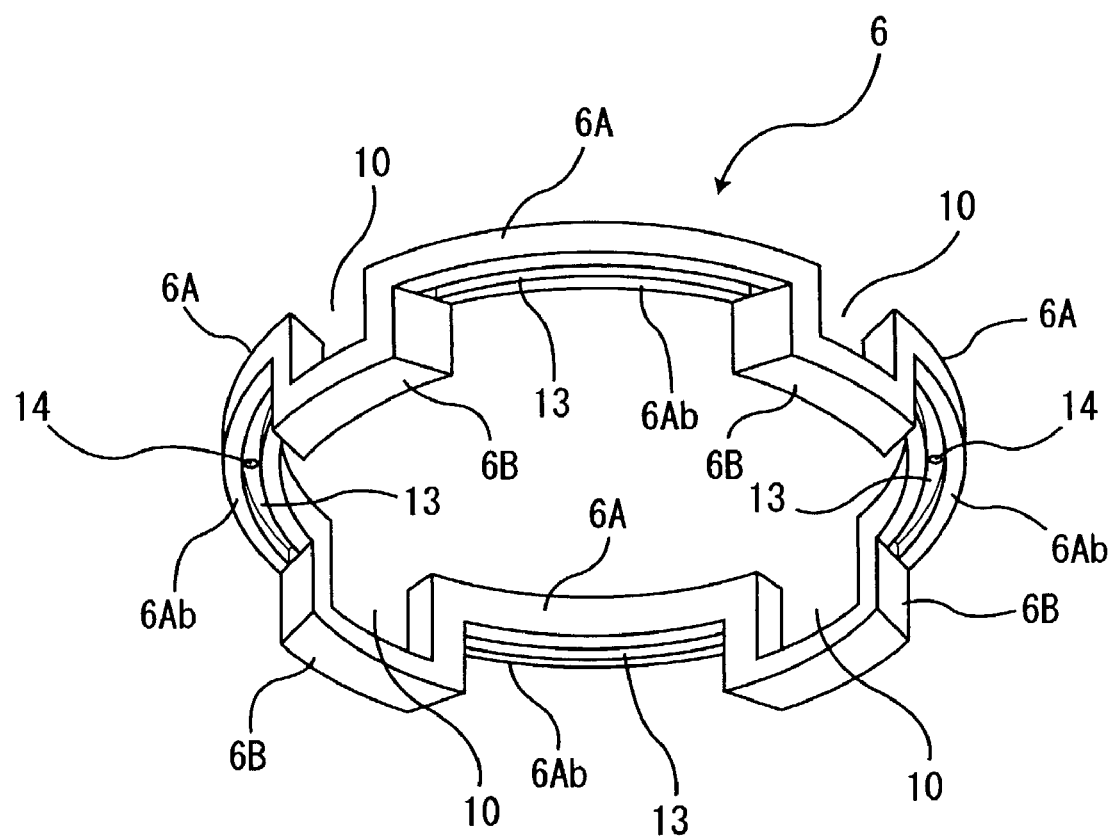
FIG. 10 is a schematic perspective of the intraocular ring assembly as viewed from the bottom side thereof.
Figure 11:
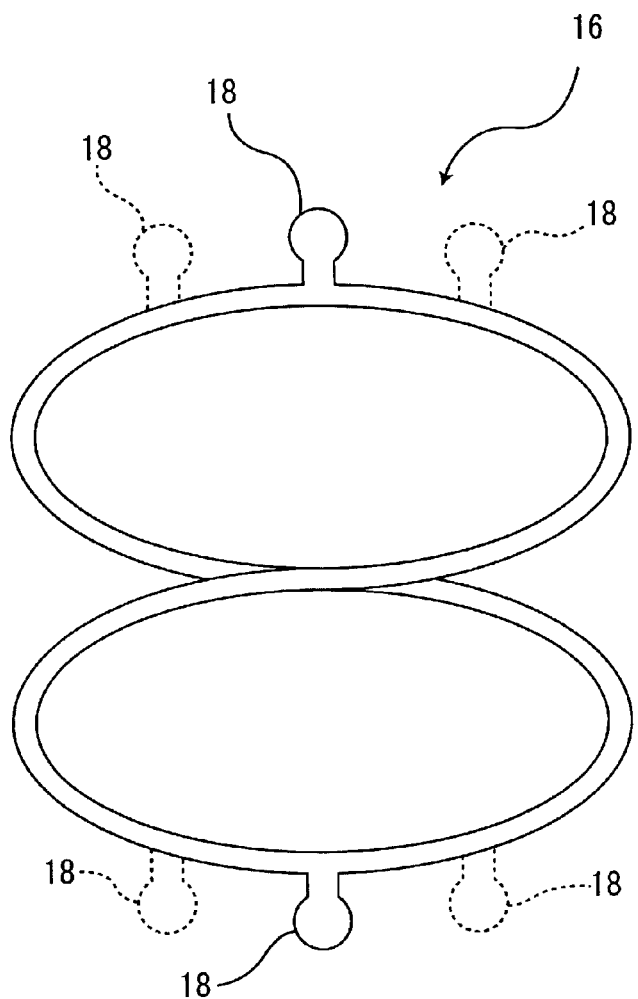
FIG. 11(A) is a plan view of an elastic biasing element used in the intraocular ring assembly.
FIG. 11(B) is a top plan view of the elastic biasing element in the FIG. 11(A)
Figure 11:
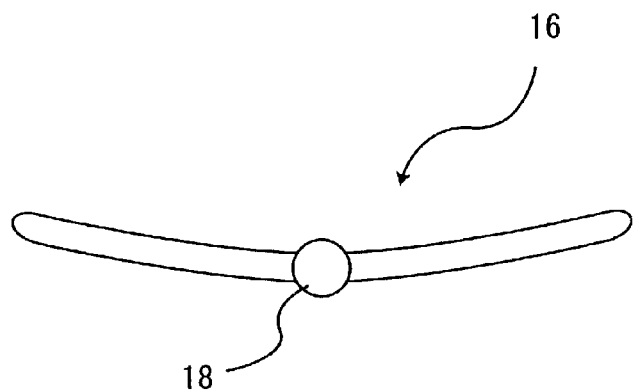

On the other hand, the second end surface 6Ab is flat, in which is formed a first securing groove 13 extending therealong in an arcuate manner, as best seen from FIGS. 8, 9 and 10. In this regard, as indicated in FIG. 8, formed in the first sectorial ring portion 6A is a spherical securing cavity 14 at a point midway of and adjacent to the securing groove 13. The spherical securing cavity 14 communicates with the groove 13 at the neck portion (N) thereof (see FIG. 12(A)) and is adapted to snappingly receive and securely engage a spherical (or dumbbell-headed) anchor piece 18 of the elastic biasing element 16, as will be specified later.

Designation 10 represents a support recession defined in each of the generally U-shaped ring portions 6B, the support recession 10 being adapted to receive and support a haptic portion 28 of intraocular lens 24 therein, as will be described.

Accordingly, it is seen that four sectorial ring portions 6A are disposed in an equidistant spaced-apart fashion along the circumference of a circle, with their respective four first end surfaces 6Au laying on a same level with one another along that circumference, whereas four support recessions 10 are alternated with the respective four sectorial ring portions 6A and thus defined in a diametrically facing relation with one another with respect to the center of ring assembly 4.

The posterior ring element 8 is shown as being simply of a circular ring shape and having outer and inner diameters equal to those of the anterior ring element 6. In contrast to the anterior ring element 6, the posterior ring element 8 has a first flat end surface 8A and a second sloped end surface 8B opposite thereto, wherein the second end surface 8B slopes downwardly as it proceeds to the center (axis) of the anterior ring element 6 (i.e. in a direction from the outer arcuate wall thereof to the inner arcuate wall thereof), as can be seen from FIGS. 1 and 3. Of course, the second end surface 8B may be formed flat. But, the illustrated sloped formation thereof is preferable to allow smooth placement of the ring element 8 within the capsular bag 34 in a moderate and intimate contact with and along the generally concave inner surfaces of capsular bag 34. This will advantageously avoid damage to the capsular bag 34. Hence, it is observed from FIG. 3 that the sloped end surfaces 6Au and 8B respectively of the anterior and posterior ring elements 6, 8 are sloped in a direction away from each other as they proceed toward a central of both two ring elements 6, 8.

In each of the first flat end surface 8A of posterior ring element 8, four second securing grooves 12 are disposed equidistantly, such that each of them extends therealong in an arcuate manner. As indicated in FIG. 8, a spherical securing cavity 15 is formed in the posterior ring element 8 at a point midway of and adjacent to the securing groove 12. The spherical securing cavity 15 communicates with the groove 12 at the neck portion (N) thereof (see FIG. 12(A)) and is adapted to snappingly receive and securely engage a spherical anchor piece 15 of the elastic biasing element 16, as will be specified later. For that purpose, the spherical securing cavity 15 is slightly larger than the spherical anchor piece 18.

As illustrated, the elastic biasing element 16 is interposed between the anterior and posterior ring elements 6, 8. With particular reference to FIGS. 11(A) and 11(B), the elastic biasing element 16 may be of a generally figure-of-eight shape, for instance, which is shown to have a pair of integral spherical (or dumbbell-headed) anchor pieces 18, 18 formed respectively in one and another opposite distal ends thereof. The purpose of this biasing element 16 is to keep the anterior and posterior ring elements 6, 8 away from each other in a resilient way. In other words, when an assembled unit of the present artificial lens kit 2 is implanted in a capsular bag 34 as in FIG. 21, the elastic biasing element 16 acts to bias the anterior ring element 6 in a direction to the anterior capsule 36, while biasing the posterior ring element 8 in a direction to the posterior capsule 38. Hence, it is to be appreciated that the four sloped end surfaces 6Au of anterior ring element 6 are kept in a close contact with the inner surface of anterior capsule 36, while the entire sloped end surface 8B of posterior ring element 8 is kept in a close contact with the inner surface of posterior capsule 38, whereby the capsular bag 34 is normally retained in a proper biconvex shape while being allowed to become adjustably flattened and inflated along the optic axis 1, in substantially the same manner as a natural crystalline lens does. Of course, the vertical length of generally figure-of-eight-shaped elastic biasing element 16 between the anterior and posterior ring elements 6, 8 may be such as to normally resiliently inflate the capsular bag 34 into a proper biconvex shape suited for individual patient.

As best seen from FIG. 11(B), the entire body of biasing element 16 may be slightly warped to assume an arcuate shape equal in curvature to the first and second arcuate securing grooves 13, 12 stated above, since the two opposite distal end portions of the biasing element 16 have to be fitted in and along the respective first and second arcuate securing grooves 13, 12. This is preferable to avoid interference with smooth contraction and expansion of the biasing element 16 per se.

The biasing or repercussive force of the biasing element 16 may be preset to a suitable degree, depending upon the elasticity of capsular bag 34 of individual patients' eye, or other conditions required in surgical operation.

As shown, the four figure-of-eight-shaped biasing elements 16 are arranged in equidistant manner between the anterior and posterior ring elements 6, 8 such that each of the biasing elements 16 is disposed between each anterior ring element sectorial ring portion 6A and the corresponding local area of posterior ring element 8.

The shape of the elastic biasing element 16 is not limited to the figure-of-eight mode in FIG. 11(A), but may be of generally "O" shape, for instance, (See FIG. 13), which has a diameter equal to the vertical length of the aforementioned generally figure-of-eight-shaped biasing element 16. In this regard, the figure-of-eight-shaped or "O" shaped biasing element may preferably be formed from a soft elastic material such as polypropylene.

Figure 12A:
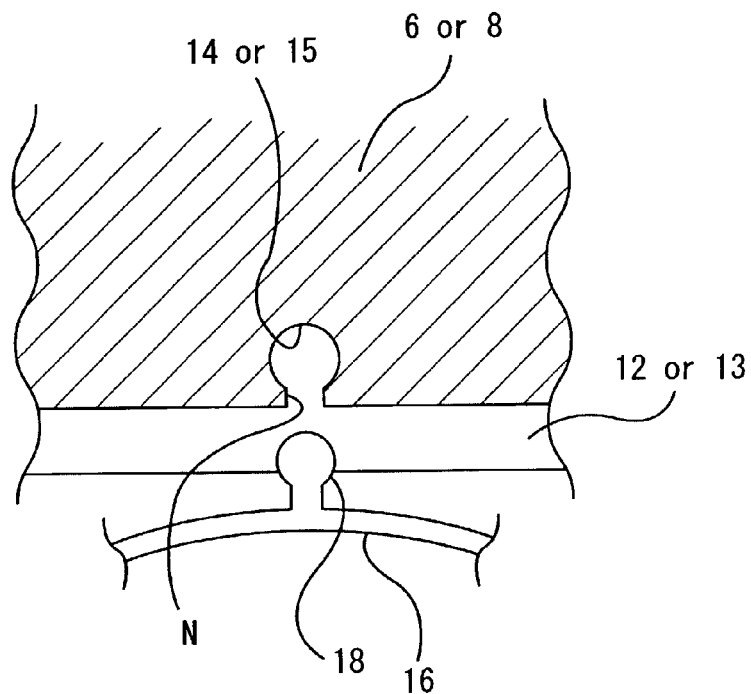
FIG. 12(A) is a fragmentary sectional view showing an engagement relation between an anchor portion of the elastic biasing element and an securing cavity formed in the intraocular ring assembly.

As understandable from FIGS. 8 and 12(A), fixation of the four biasing elements 16 (of figure-of-eight shape) between the anterior and posterior ring elements 6, 8 is such that two opposite arcuate distal end portions of each biasing element 16 are respectively fitted and engaged in the first and second securing grooves 13, 12, while the two spherical anchor pieces 18, 18 of each biasing element 16 are snappingly anchored in the spherical securing cavity 14 of the anterior ring element 6 and the spherical securing cavity 15 of the posterior ring element 8, respectively. In this way, both two ring elements 6, 8 are coupled together via the four biasing elements 16 against separation from each other, thereby forming an intraocular ring assembly 4, wherein the biasing elements 16 themselves are prevented against dislocation from their respective securing points. As an alternative to such anchoring and securing means, any other suitable coupling and fitting members or engagement members may be provided to securely dispose the biasing elements 16 between the anterior and posterior ring elements 6, 8.

The first and second securing grooves 12, 13 may be formed in an appropriate shape and size, depending on the configuration of the elastic biasing element 16. In the case of the illustrated figure-of-eight mode having arcuate distal end portions, it is preferable to form two groove extensions in the respective two extremities of each securing groove, thereby to allow both two lateral arcuate portions of the biasing element 16 to become protrudent outwardly and stored partway in the respective two groove extensions, when the biasing element 16 is subjected to elastic depression or contraction. Namely, as best indicated in FIG. 8, each first securing groove 13 may be formed with a pair of groove extensions 13A, 13A in the respective two extremities thereof, while on the other hand, each second securing groove 12 be formed with a pair of groove extensions 12A, 12A in the respective two extremities thereof. By being so formed, the biasing elements 16 are freely contractible and expandable without interference with the grooves 12, 13 along a rectilinear direction, which advantageously insures rectilinear coaxial displacement of both anterior and posterior ring elements 6, 8. This is applicable to any configuration of the elastic biasing element that has arcuate end portions, including "O" shape (similar to the integral "O" shape as in FIG. 13). Hence, when the intraocular ring assembly 4 is implanted in the capsule bag 34, such rectilinear biasing arrangement insures to allow rectilinear movement of those two ring elements 6, 8 in a coaxial relation with the capsular bag 34 along the optic axis 1.

Figure 12B:
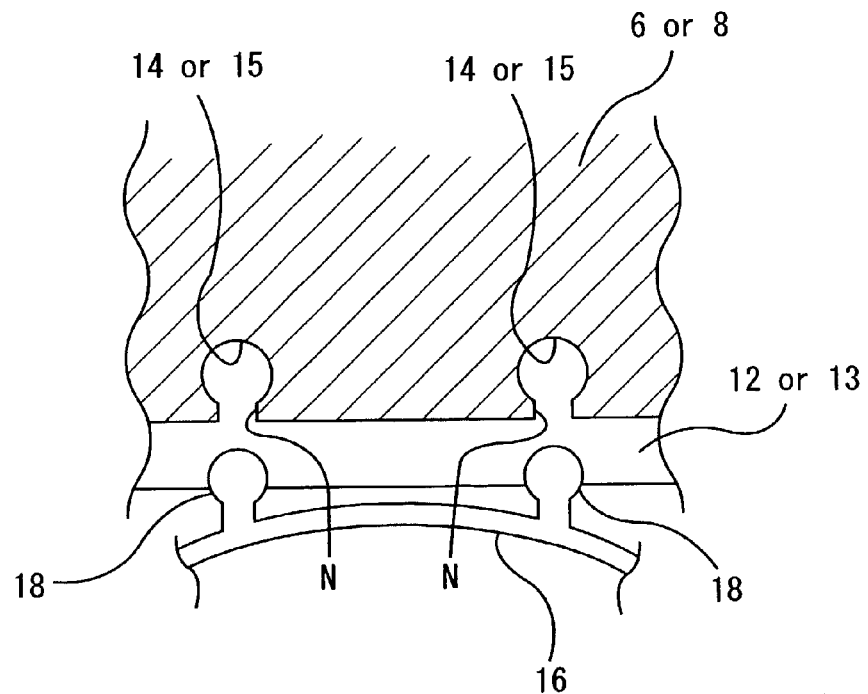
FIG. 12(B) is a fragmentary sectional view showing engagement relations among two anchor portions of the elastic biasing element and two securing cavities formed in the intraocular ring assembly.
Figure 13:
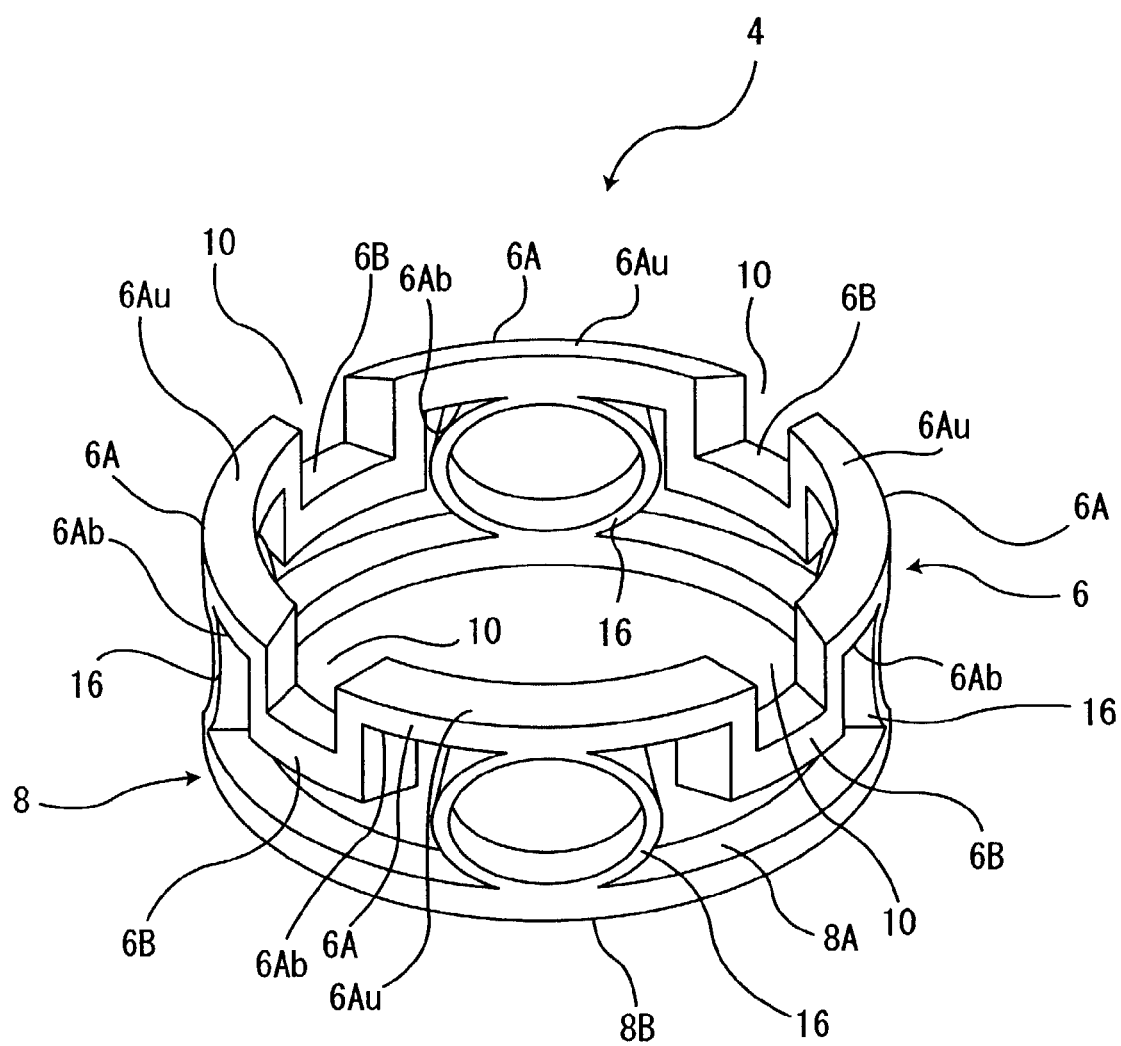
FIG. 13 is a schematic perspective view showing an alternative exemplary mode of the intraocular ring assembly in accordance with the present invention.
Figure 14:
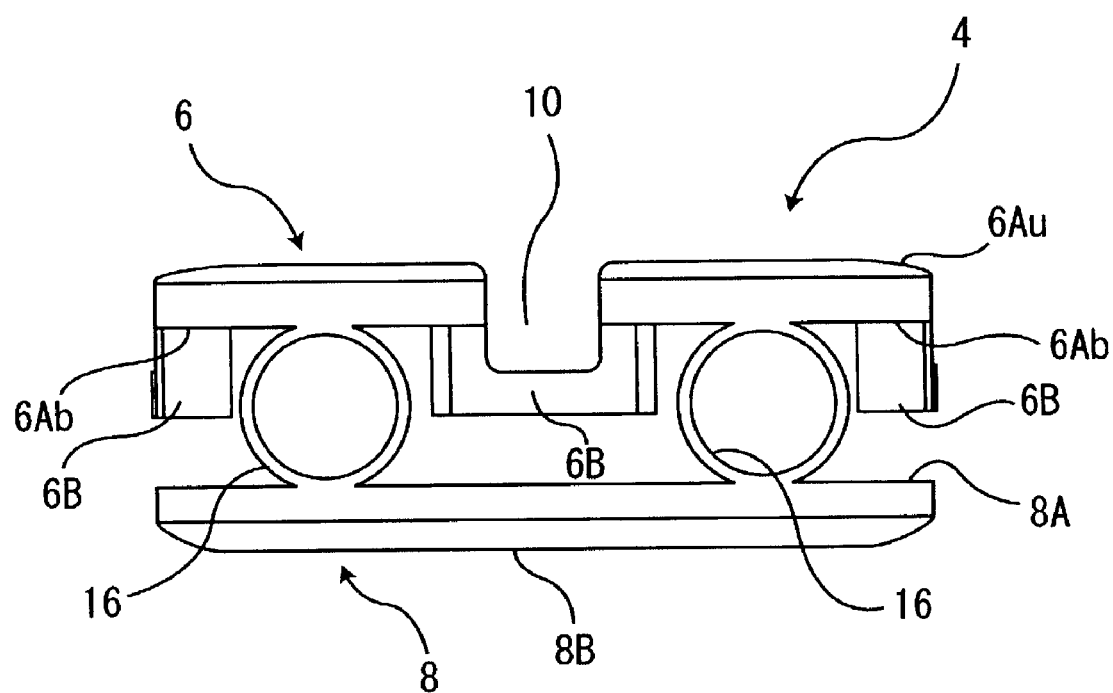
FIG. 14 is a side elevational view of such alternative mode of intraocular ring assembly shown in the FIG. 3.

In this context, as indicated by the phantom lines in FIG. 11(A) and understandable from FIG. 12(B), a pair of spherical (dumbbell-headed) anchor portions 18, 18 may be formed in each of the two distal arcuate end portions of biasing element 16.

And, one pair of spherical securing cavities 14 may be formed in the anterior ring element 6 (i.e. in each sectorial ring section 6A), while another pair of spherical securing cavities 15 be formed in the posterior ring element 8 in such dimensions as to snappingly receive and securely engage the corresponding two spherical anchor portions 18, 18. This is not limitative, but a desired number of such securing elements (14, 15, 18) may be provided to attain a more robust and stable structure of the intraocular ring assembly 4.

It is noted that the elastic biasing element 16, be it of the figure-of-eight shape or of a circular shape, may be formed directly and integrally between the anterior and posterior ring elements 6, 8, without using the aforementioned anchoring or securing means (e.g. at 14, 15 and 18). In this regard, as suggested in FIGS. 13 and 14 for example, the elastic biasing element 16 may be formed in a generally "O" shaped configuration and interposed integrally between the anterior and posterior ring elements 6, 8. In this embodiment, four generally "O" shaped elastic biasing elements 16 are arranged integrally between the respective four first sectorial ring portions 6A of anterior ring element 6 and the flat surface 8A of posterior ring element 8. That is, as shown, each of those four biasing elements 16 is at one end portion thereof integrally and continuously formed with each first sectorial ring portion 6A of anterior ring element 6 and is at another end portion thereof integrally and continuously formed with the posterior ring element flat surface 8A. Of course, the diameter of each generally "O" shaped biasing element 16 is such a degree as to normally resiliently inflate the capsular bag 34 into a proper biconvex shape suited for individual patient as described earlier.

Figure 15:
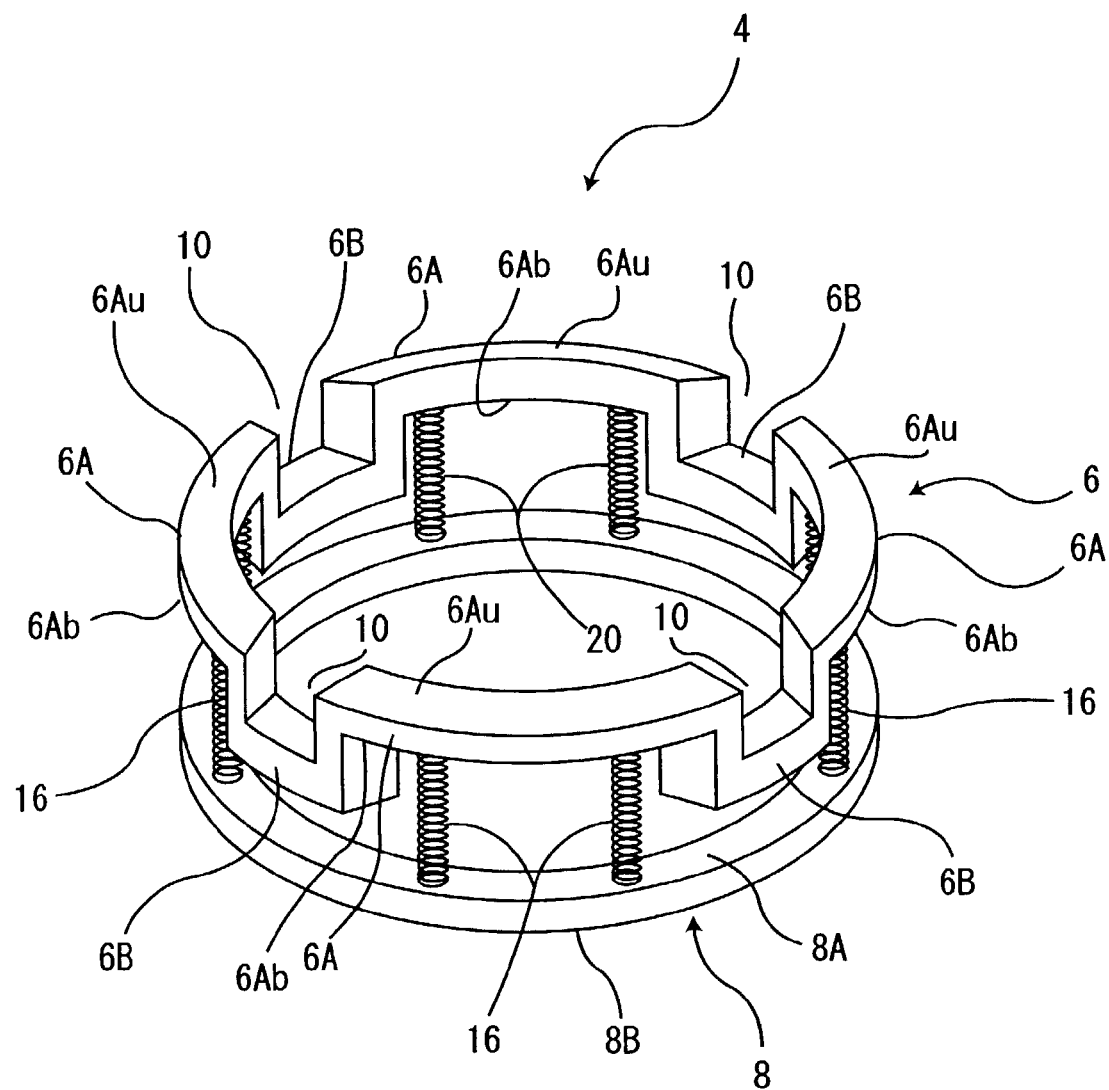
FIG. 15 is a schematic perspective view showing another alternative mode of the intraocular ring assembly.
Figure 16:
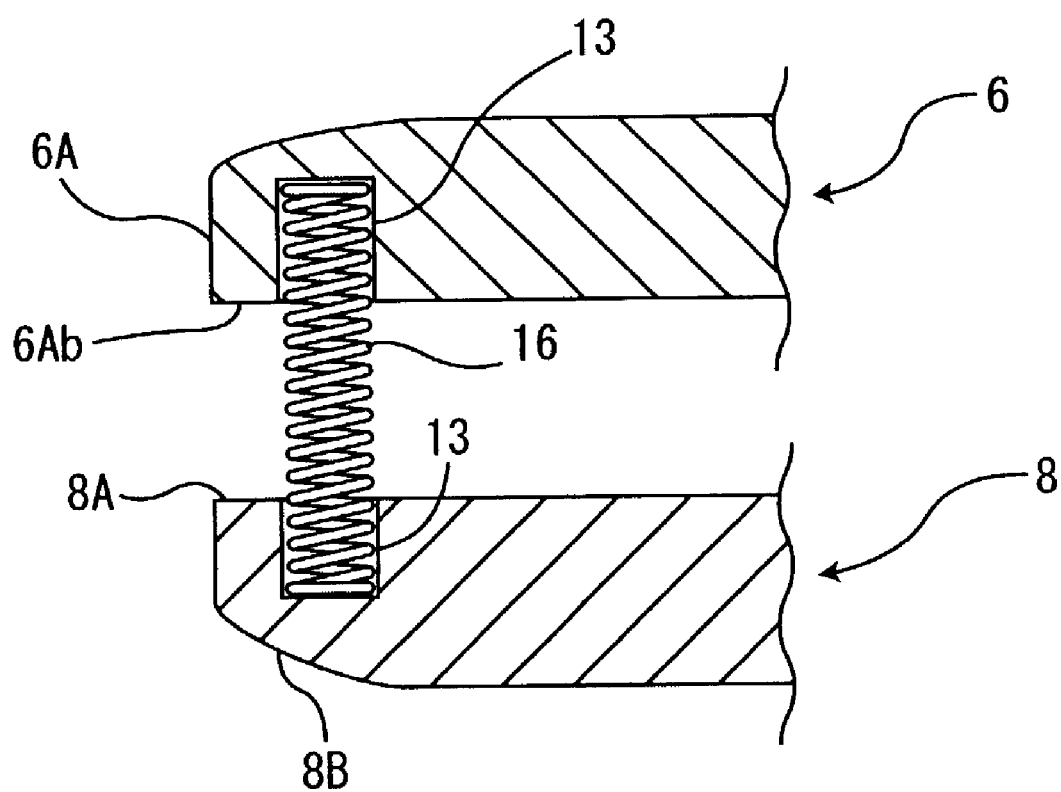
FIG. 16 is a fragmentary sectional view of the intraocular ring assembly shown in the FIG. 15, which shows a coil spring provided therein.

Or, alternatively, as suggested in FIGS. 15 and 16, the elastic biasing element 16 may be a coil spring. According to this particular mode, four sets of two rectilinearly extending coil springs 16 are disposed in equidistant manner between the anterior and posterior ring elements 6, 8 such that the paired coil springs 16 are each disposed between each generally U-shaped ring section 6B and the corresponding local area of posterior ring element 8. Further, as best shown in FIG. 16, a first securing hole 12 is formed in the end surface 8A of posterior ring element 8 in place of the afore-said first securing groove 12, whereas on the other hand, a second securing hole 13 is formed in the end surface 6Ab of each first sectorial ring portion 6A in place of the afore-said second securing groove 13. Accordingly, as shown, each coil spring 16 is at its one end firmly secured in the first securing hole 12, while being at its another end firmly secured in the second securing hole 13. The coil spring 16 may be formed from a suitable metallic material with elastic property, for instance. Of course, the vertical length of each coil spring 16 is of such a degree as to normally resiliently inflate the capsular bag 34 into a proper biconvex shape suited for individual patient as described earlier.

Figure 17:
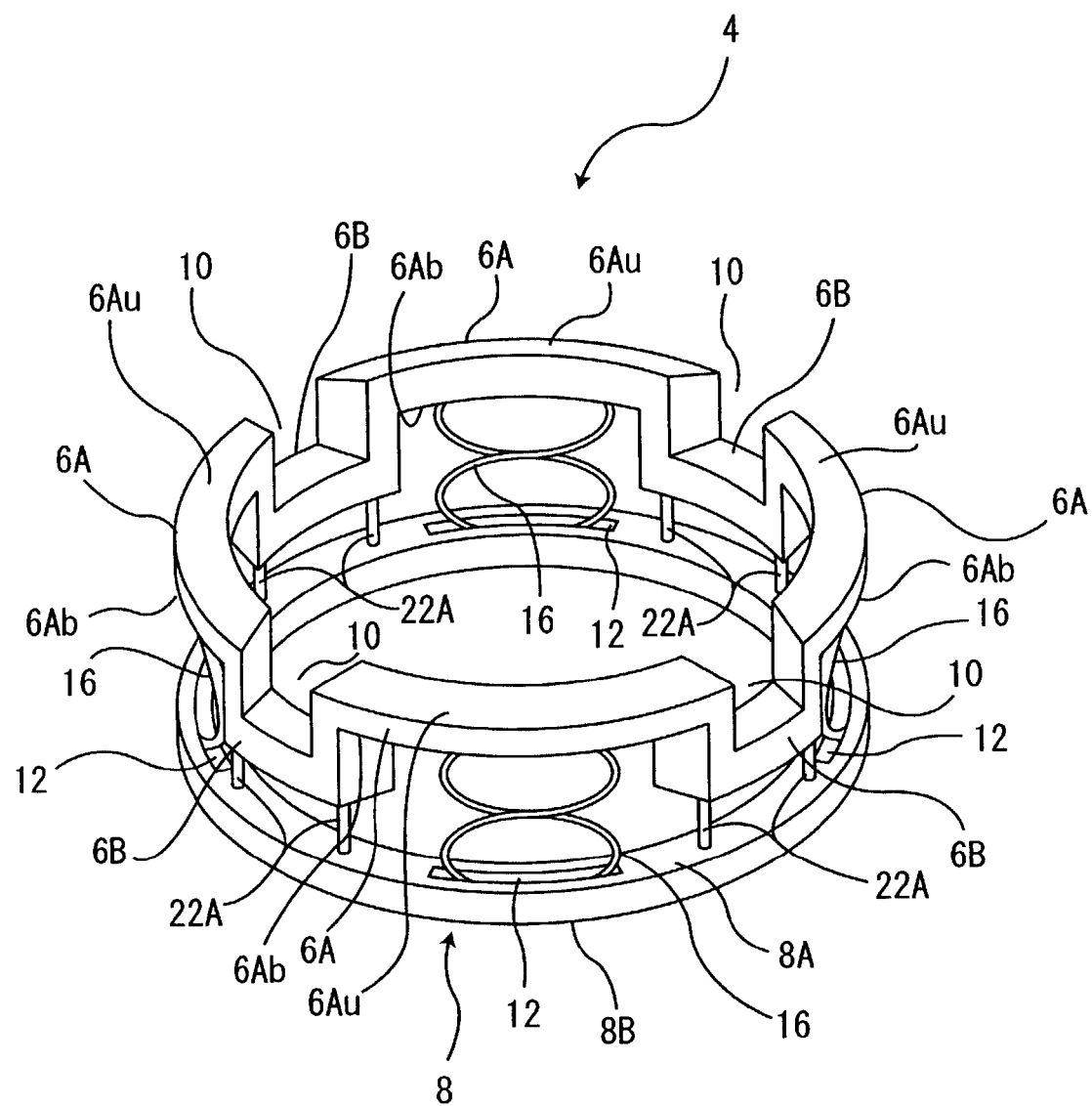
FIG. 17 is a schematic perspective view showing still another alternative mode of the intraocular ring assembly.
Figure 18:
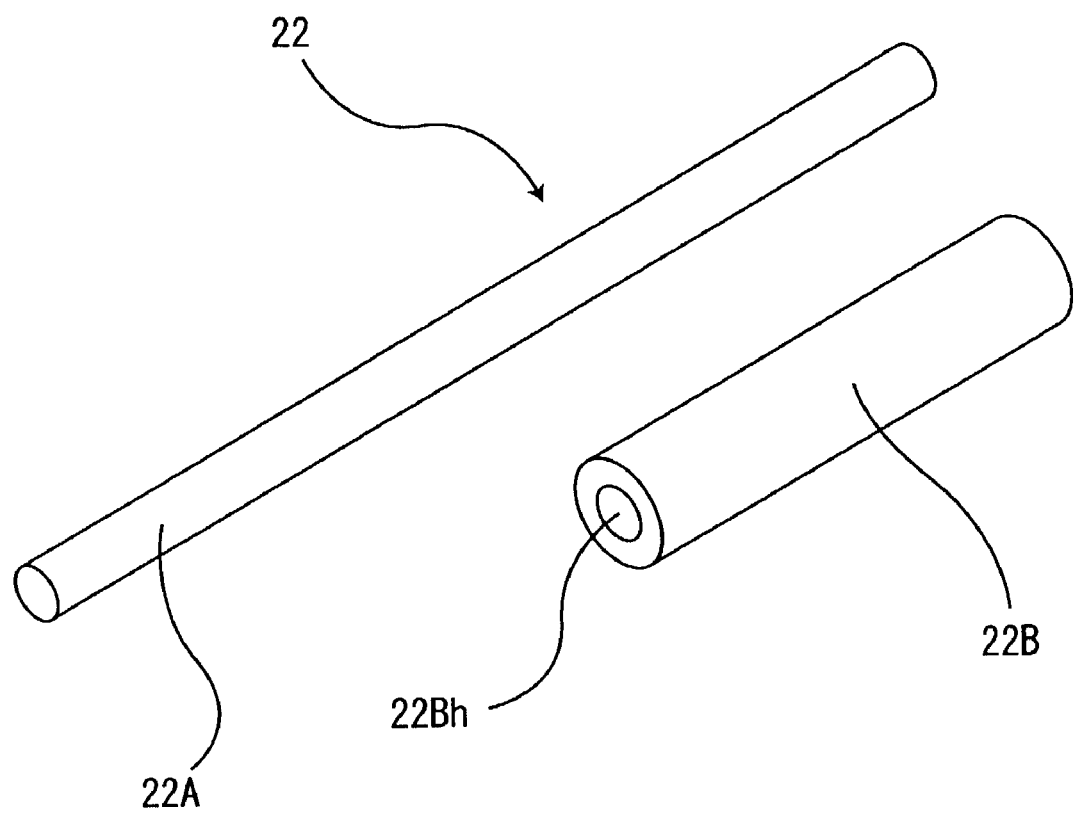
FIG. 18 is a schematic explosive perspective view showing one exemplary mode of a guide element provided in the intraocular ring assembly, which shows a cylindrical guide member and a guide rod.
Figure 19:
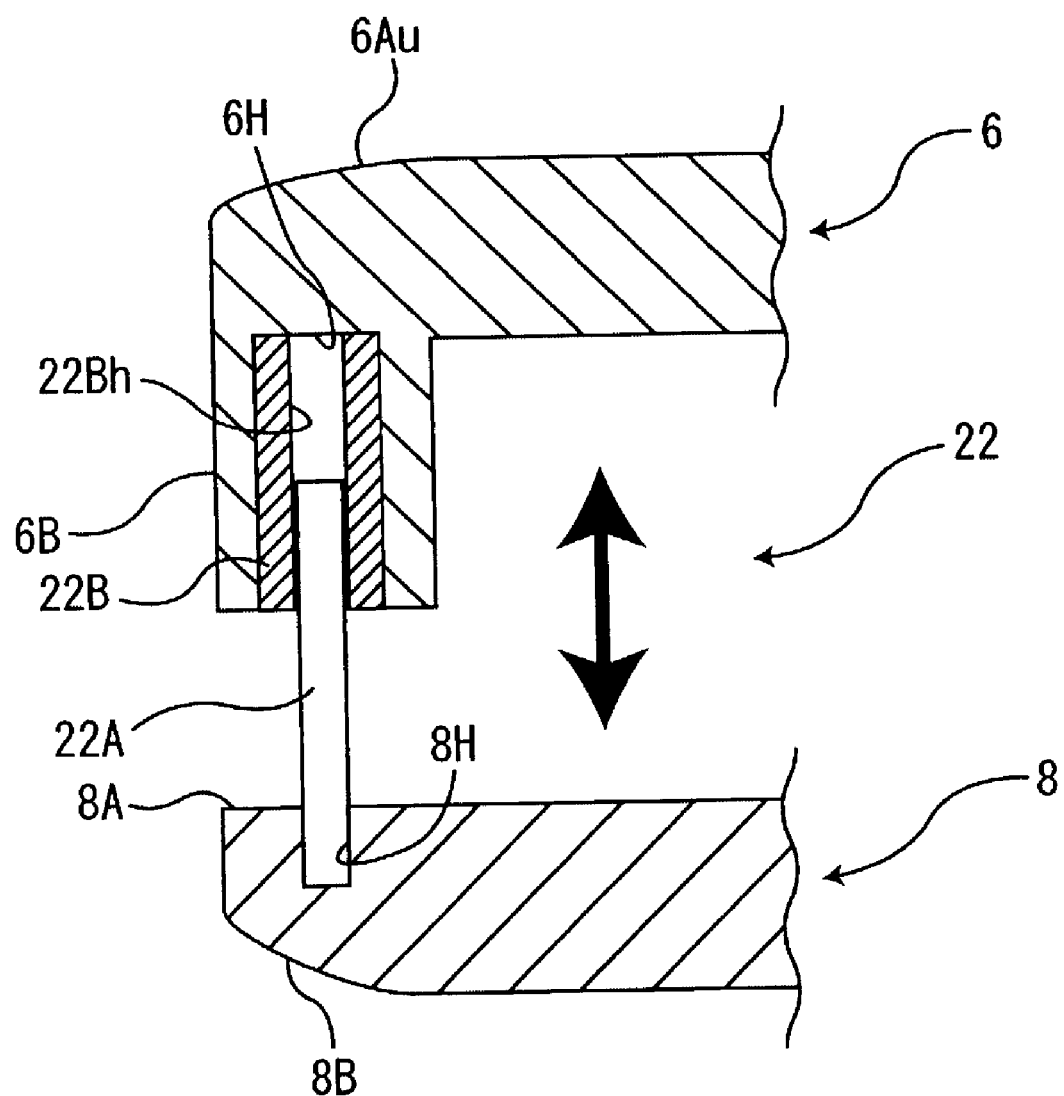
FIG. 19 is a fragmentary sectional view which explanatorily shows action of such one mode of guide element shown in the FIG. 18.

In accordance with the present invention, a guide means 22 may be incorporated in the intraocular ring assembly 4 to assist in rectilinear coaxial movement of the anterior and posterior ring elements 6, 8. Reference is made to FIG. 17 which depict one exemplary mode of the guide means generally indicated by the parenthetic designations (22), which is interposed between the anterior and posterior ring elements 6, 8. In this particular mode, as understandable from all FIGS. 17, 18 and 19, four sets of two guide means 22, 22 are arranged in equidistant manner between the two ring elements 6, 8 such that each of the paired guide means 22, 22 is disposed between each generally U-shaped ring portion 6B and the corresponding local area of posterior ring element end surface 8A. As best shown in FIGS. 18 and 19, each of the illustrated guide means 22 basically comprises a guide rod member 22A and a cylindrical guide member 22B having a through-bore 22Bh formed therein and further includes a cylindrical cavity 6H formed in the anterior ring element 6 (i.e. in the generally U-shaped ring portion 6B). As understandable from FIG. 19, the guide rod member 22A is at its one end portion fixed in a securing hole 8H formed in the posterior ring element 8, projecting vertically therefrom. Each of the cylindrical guide member 22B has an outer diameter generally equal to the inner diameter of the cylindrical cavity 6H and also has a whole length generally equal to that of the cavity 6H. The cylindrical guide member 22B is fixedly provided in the cylindrical cavity 6H. Another end portion of the guide rod member 22A is slidably inserted in the through-bore 22Bh of cylindrical guide member 22B. Accordingly, as indicated by the arrow in FIG. 18, the anterior and posterior ring elements 6, 8 are positively assisted by the guide means 22 in their precise coaxial rectilinear movements toward and away from each other. It is noted that this guide means 22 may be formed in any other suitable configuration insofar as it serves to guide both two ring elements 6, 8 in the coaxial rectilinear direction. Moreover, it may be so arranged that a rectilinearly extending coil spring, similar to the one (16) described earlier, is secured in the cylindrical guide through-bore 2Bh and cavity 6H to apply a resilient biasing force to the guide rod member 22A, thereby achieving both biasing and guiding effects collectively in one localized small area for each of plural guide means 22.

Figure 20:
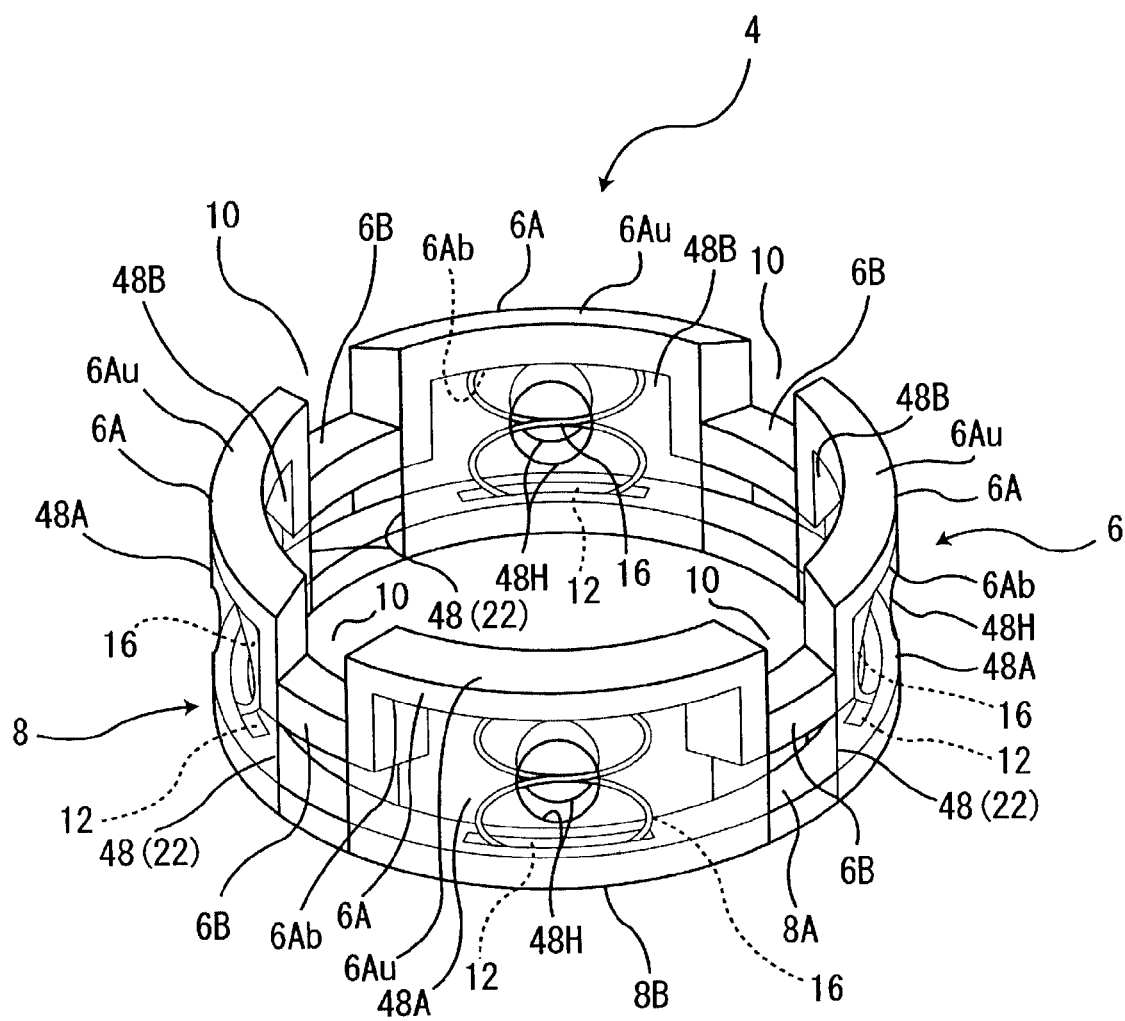
FIG. 20 is a schematic perspective view showing yet still another alternative mode of the intraocular ring assembly, which utilizes a plurality of thin plate materials as the guide element.

FIG. 20 shows another alternative embodiment of the guide means generally indicated by the parenthetic designation (22), according to which, the guide means may be an elastic thin plate material 48 which has a circular hole 48H formed centrally thereof.

The elastic thin plate material 48 per se may be formed from a thin sheet of transparent plastic material with a proper resilient bendable property. In the illustrated embodiment, a pair of outward and inward elastic thin plate materials 48A, 48B are provided. Total four sets of such paired plate materials 48A, 48B are connected between the anterior and posterior ring elements 6, 8 in such a manner that the four sets of the paired plate materials 48A, 48B are disposed at the four first sectorial ring portions 6A, respectively. As viewed from FIG. 20, each outward elastic thin plate material 48A is firmly attached at the upper region thereof to the outward arcuate lateral surface of the corresponding one of the four first sectorial ring portions 6A of anterior ring element 6, and is also firmly attached at the lower region thereof to the outward arcuate lateral surface of posterior ring element 8. On the other hand, each inward elastic thin plate material 48B is, at the upper region thereof, firmly attached to the inward arcuate lateral surface of corresponding one of the four first sectorial ring portions 6A, while being, at the lower region thereof, firmly attached to the inward arcuate lateral surface of posterior ring element 8. The provision of the holes 48H is effective in allowing the two plate materials 48A and 48B to be easily and smoothly bendable outwardly in a direction away from each other, and also insuring smooth flow of air and aqueous humor between the paired plate material 48A, 48B.

Figure 4:
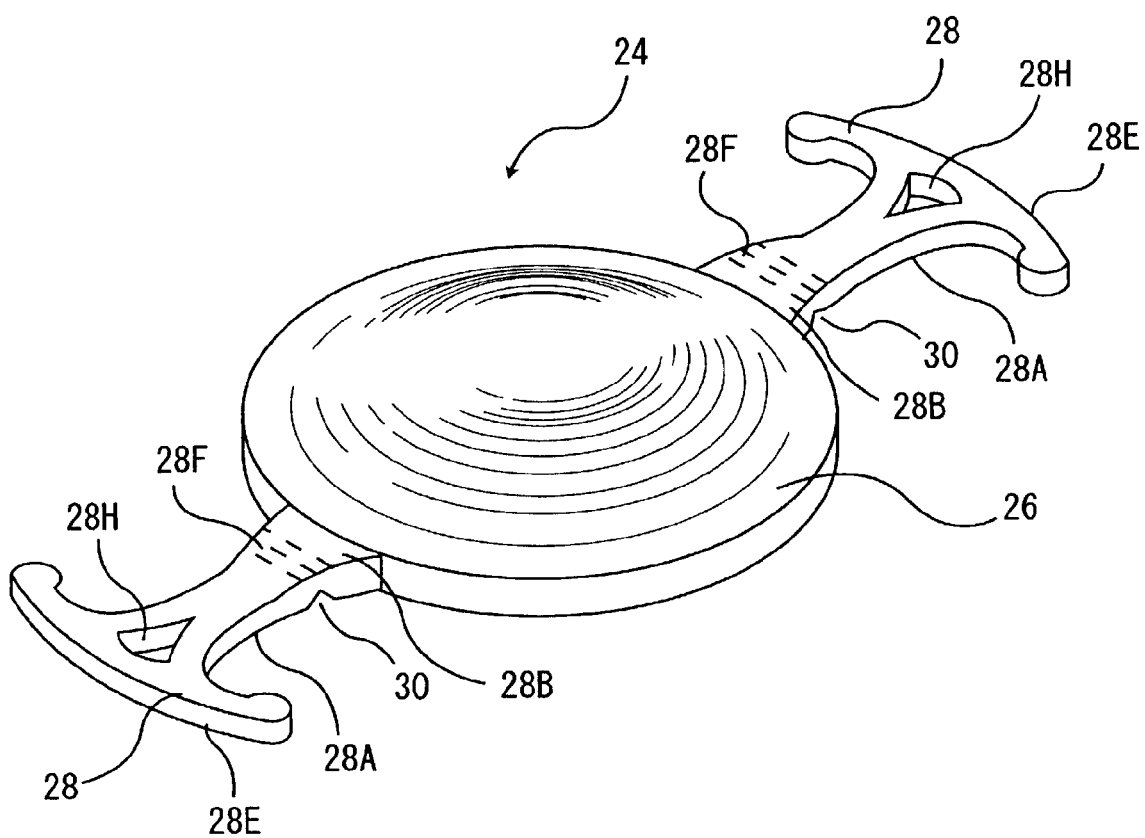
FIG. 4 is a schematic perspective view of one exemplary mode of an intraocular lens to be used in the artificial lens kit or intraocular ring assembly of the present invention.
Figure 5:
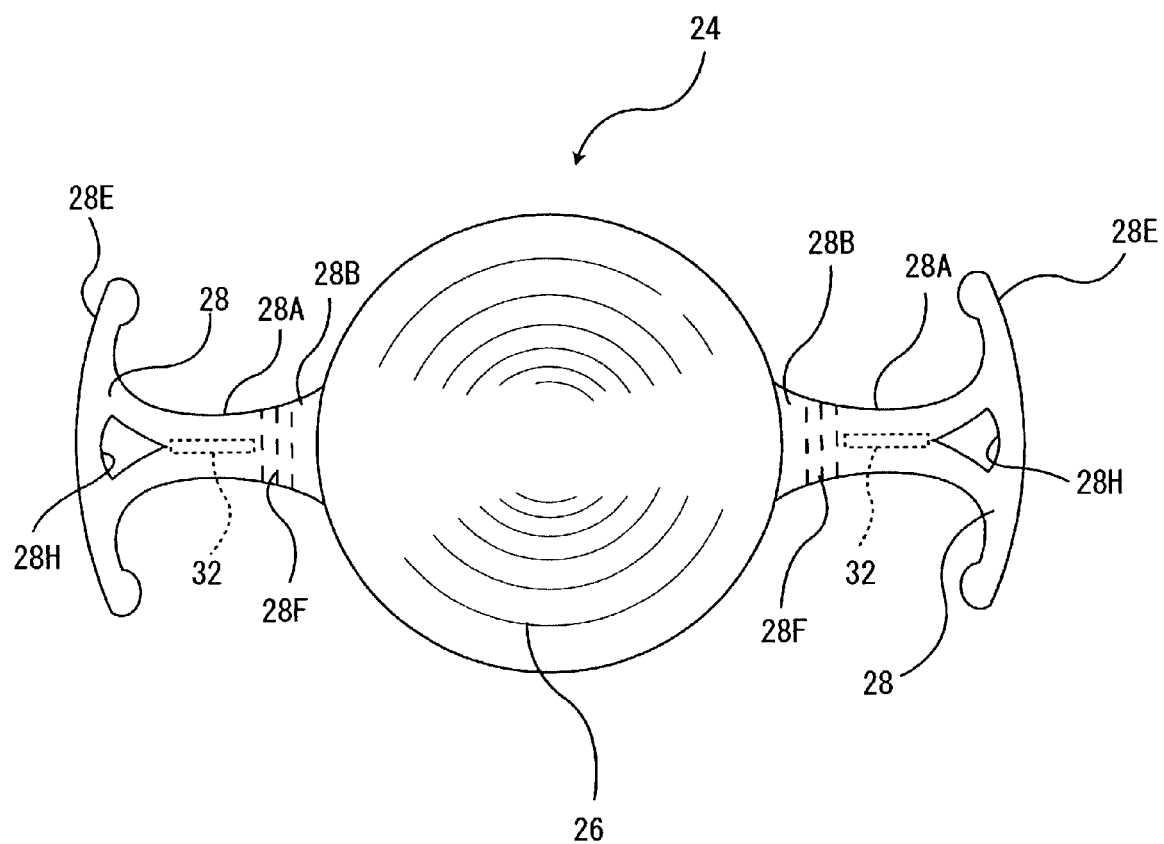
FIG. 5 is a front view of the intraocular lens.
Figure 6:
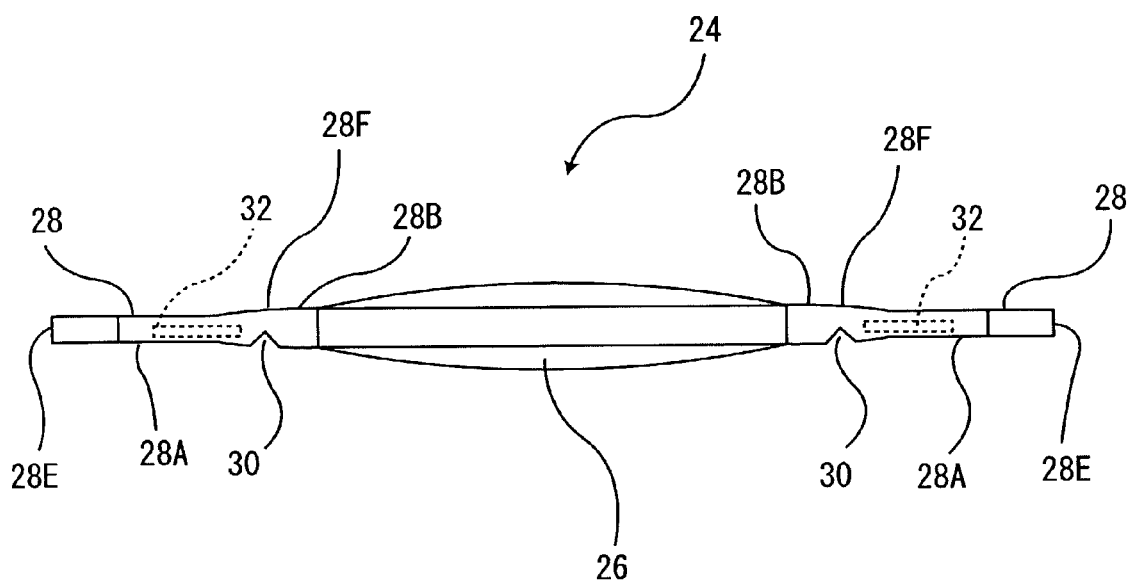
FIG. 6 is a side elevational view of the intraocular lens.
Figure 7:
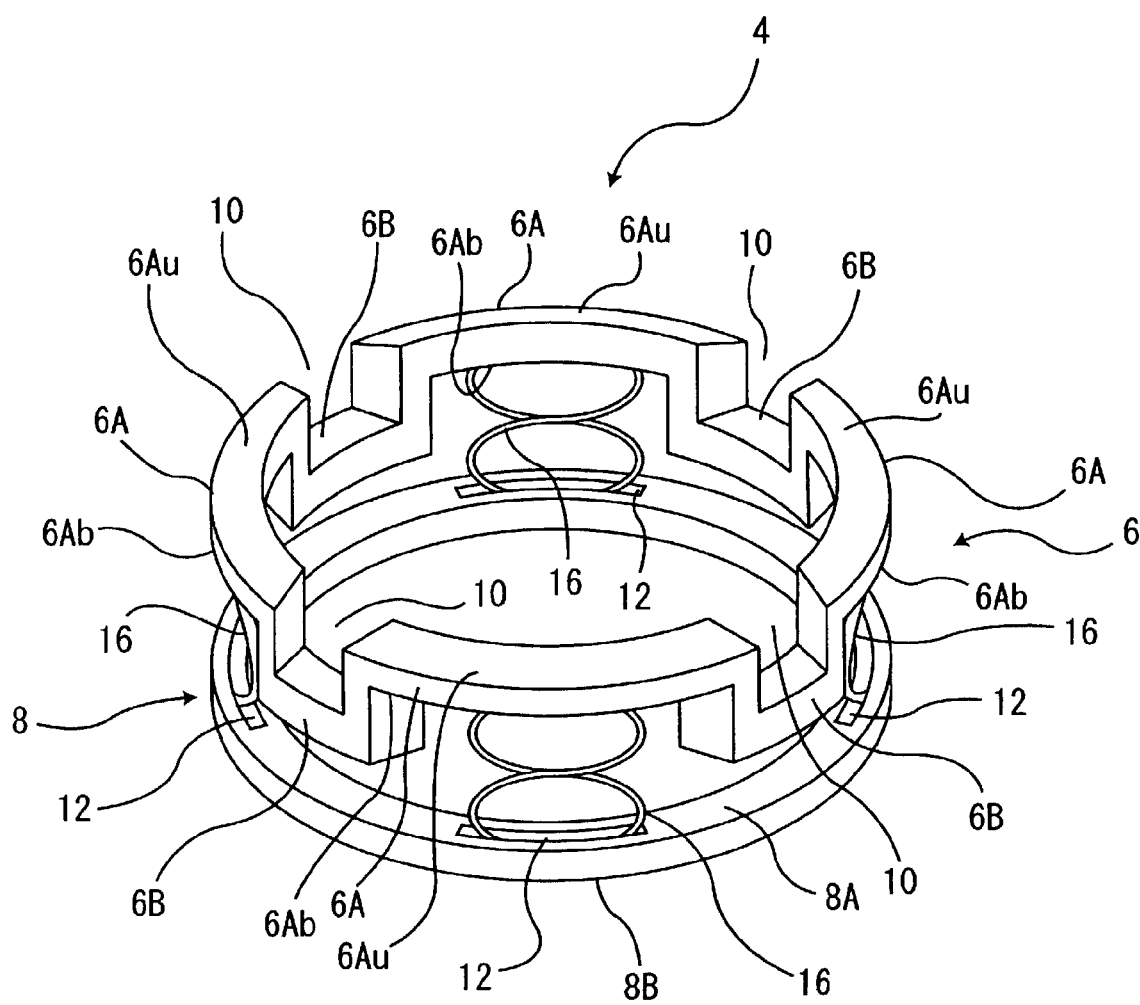
FIG. 7 is a schematic perspective view showing one exemplary mode of intraocular ring assembly in accordance with the present invention.

Reference being now made to FIGS. 4, 5 and 6, there is illustrated one preferred embodiment of the intraocular lens, as generally designated by 24, which is to be supported in the above-described intraocular ring assembly 4. The intraocular lens 24 is basically comprised of an optic portion 26 and a pair of haptic portions 28, 28. As shown, the optic portion 26 is of a generally biconvex lens configuration having a circumferential end, and the two haptic portions 28, 28 are integrally connected with the circumferential end of optic portion 26, projecting outwardly therefrom in a diametrically opposed direction relative to the center of the optic portion 26. Both optic and haptic portions 26, 28 may preferably be formed from a soft elastic material, such as acrylic or silicon. But, this is not limitative and any other suitable material may be used to form them, taking into account the conditions and requirements in implanting the lens 24 in a patient's eye. Also, the optic and haptic portions 26, 28 should not necessarily be of a same material, but may each be of a different proper material. It is noted that the intraocular lens 24 may be of any normally available type that can be mounted in the intraocular ring assembly 4 and has the bendable haptic portions 28 which will be described later. With regard to the optic portion 26, it is not limited to the illustrated one, but may be formed in any suitable lens configuration having a proper thickness so as to attain an optimal refractive power on the basis of a diagnostic data on individual patient's eyes.

The illustrated two haptic portions 28 are each of a generally "T" shape which basically comprises: a base portion 28B integrally connected with the circumferential end of optic portion 26; a curved distal end 28E; and a generally rectilinear body portion 28A defined between the base portion 28B and curved distal end 28E, wherein it is seen that the body portion 28A has a divergently widened region near to the distal end 28E. Preferably, a generally triangular or sector-shaped hole 28H is formed in such divergently widened region of the body portion 28A in the proximity of the curved distal end 28E. Also, preferably, the curved distal end 28E is so formed to extend a certain distance along the circumference of a circle whose center is at the center of the optic portion 26. With this structure, both two end portions of the haptic portion 28 are provided with a proper elasticity to render themselves resiliently deformable according to different shape and size of capsular bag 34, so that the whole intraocular lens 24 can be smoothly set in position and retained within a different capsular bag 34 of different patient's eye. In this respect, preferably, the whole size of the two haptic portions 28 is slightly larger than the diameter of capsular bag 34 to attain a positive resilient attachment of the former (28) to an inside of the latter (34). Moreover, due to its circumferential elongation, each curved distal end 28E increases an area for contact with and along the inner surface of capsular bag 34 corresponding to the equator 40 thereof. This allows the entirety of intraocular lens element 24 to be adjustably and stably fitted in any different diameter of capsular bag 34, and also makes the elastic action of both two haptic portions 28 more sensitive to a contour change of the capsular bag 34 being caused by the contraction and relaxation of zonule (at 42 in FIG. 21).

As can be seen from FIGS. 4 to 6, each haptic portion 28 has a bendable area 28F defined at a point adjacent to the base portion 28B thereof, so that the haptic portion 28 per se may be resiliently bended or folded in vertical direction relative to the optic portion 26. To facilitate the ease of such bending action, a bendable means is provided in proximity to the base portion 28B. As such bendable means, for instance, a transverse cutout 30 is formed in one side of that bendable area 28F adjacent to the base portion 28B in such a fashion as to assume a generally inverted-V-shaped cross-section extending transversely of the haptic portion 28. Accordingly, it is to be appreciated that, when both two haptic portions 28 are pressed toward each other in a direction inwardly of the optic portion 26, they are quickly bended at their respective cutouts 30 in one direction (i.e. a direction toward a side where those particular cutouts 30 are situated) relative to the optic portion 26, which in turn causes that optic portion 26 to displace in the same direction as that one direction (as can be seen from FIG. 23) Conversely, when the two haptic portions 28 are pulled outwardly from such bended state in a direction away from each other, they are extended outwardly on the same rectilinear horizontal line from the optic portion 24 (as can be seen from FIG. 22). It is noted that the cutout 30 is just one example of bendable means for facilitating the ease with which the bendable area 28F of haptic portion 28 is bended to cause the displacement of optic portion 26, and such bendable means may be embodied in any other suitable manner, including hinges or the like.

A reinforcement core element 32 is preferably embedded in the rectilinear body portion 28A of haptic portion 28. Provision of such core element 32 effectively serves to reinforce the haptic portion 28 and prevent the same from being bent together with the above-stated bending action of bendable area 28F. This is also effective in transmitting most of force applied to the haptic portion 28 directly to the cutout 30, thereby inducing more smooth bending action of the haptic portion 28 relative to the cutout 30. The core element 32 is preferably formed from such a rigid material as a hard plastic or metallic material. The artificial lens kit 2 may preferably include a fibronectin or fibronectin-like substance. Namely, it is preferable to apply an appropriate amount of suitable fibronectin or fibronectin-like substance to the haptic portions 28 in advance, so that, in practical surgical operation to place the intraocular lens element 24 in the capsular bag 34, both two haptic portions 28 may be positively adhered via the fibronectin or fibronectin-like substance to and along the inner surface regions of capsular bag 34 corresponding to the equator 40 thereof, wherein the fibronectin or fibronectin-like substance induces a biological fibrous adhesion of the haptic portion 28 to such equator regions of capsular bag 34. Here, the term, "fibronectin-like substance" is defined as a substance containing a fibronectin, a fibronectin-related substance, or any other substance exhibiting the same fibrous adhesion effect as the fibronectins. Referring to FIG. 2, as indicated by the character Fb, a suitable fibronectin or fibronectin-like substance may be applied to the partial end region of each haptic portion 28. Or, alternatively, as indicated by the character Fb', the fibronectin or fibronectin-like substance may be applied to a substantially whole of each haptic portion 28. Whether the fibronectin (or fibronectin-like substance) should be applied to the partial end region of haptic portion 28 or applied to a substantially whole of the same is dependent upon the conditions and dimensions of patient's lens capsule in order to insure an optimum adhesion of the haptic portion 28 to the capsular bag equator region (at 40).

In accordance with the present invention, the above-described intraocular ring assembly 4 and intraocular lens 24 constitute one artificial lens kit 2 usable for implantation in the capsular bag 34. In the shown embodiment, the two haptic portions 28 may be set in place in the corresponding selected two of the four support recessions 10 of the intraocular ring assembly 4. Of course, while not shown, it is optionally possible to define only two support recessions 10 in the ring assembly 4 so as to receive and support the two haptic portions 28, respectively. But, the illustrated formation of four equidistant support recessions 10 is superior to such formation of only two support recessions 10. This is because, when putting together the lens 24 and ring assembly 4 within the capsular bag 34, it is easier and quicker to drop and set the two haptic portions 28 of the lens 24 in the corresponding two of the four recessions 10 than in the only two respective recessions 10, due to the fact that, in the case of such four recessions 10, the distance between the adjacent two recessions 10 is quite small and therefore requires a less amount of rotation of the lens 24 upon the ring assembly 4 to drop and set the two haptic portions 28 in selected two of the four recessions 10, respectively. However, the number and shape of the support recessions 10 are not limitative and may be varied, depending on the configuration of haptic portions 28 to be received therein.

In this context, a brief description will be made of an after-cataract. In the case of extracapsular cataract extraction procedure, it is with a high frequency that an opacification will occur along the capsular bag 34 postoperatively and the opacification may progress on to a pupil region of the eye (i.e. a point adjacent to the center of capsular bag 34), which may result in a decreased visual acuity. This symptom is what is called "after-cataract". Such decreased visual acuity due to the after-cataract is a critical problem among ophthalmologists, but, there is no effective measure to prevent the after-cataract.

The after-cataract can be classified into the following two typical cases: "fibrous opacification" and "Elschnig's pearls". The fibrous opacification (or fibrosis) is a state where the posterior capsule area of capsular bag 34 becomes white and cloudy due to the production of extracellular matrix such as collagen. In other words, after cataract operation, a part of the epithelial cells of natural crystalline lens is transformed into myofibroblast-like cells which in turn produce a great amount of the extracellular matrix composed of fibrous tissues (including "type I" collagen and "type II" collagen). Thus, the extracellular matrix so produced causes the fibrous opacification (fibrosis) in a part of posterior capsule 38. More specifically stated, in cataract operation, an incision is first made to the anterior capsule of lens 36 in a circular manner relative to the center thereof (i.e. anterior capsulotomy), the anterior capsule 36 having a lens epithelial cell thereon (the lens epithelial cell exists only in the anterior capsule). Hence, defined in the anterior capsule 36 is a circular edge (see 44E in FIG. 21) which is indeed a place where the lens epithelial cell will be transformed into myofibroblast-like cell. In the early postoperative stage, since the anterior capsule 36 is slack and folded inwardly thereof due to the circular incision, a whole of the anterior capsule 36 starts to be gently adhered by fibrin and other factors to the posterior capsule 38. In most cases, such adhesion occurs in the equator region of capsular bag 34 and develops toward the circular edge 44E of anterior capsule 36, after which, under the influence of so developed adhesion, the lens epithelial cell remnant in the anterior capsule 36 proliferates while being transformed into myofibroblast-like cell, and also, some other cells are subjected to trans-differentiation. These transformed and transdifferentiated cells produce a great amount of fibrous extracellular matrices which tend to strongly adhere that circular edge 44E to and along the capsular bag equator region at 40. Thus, fibrous opacification (or fibrosis) is generated from such adhered region or fibrous extracellular matrices and develops therefrom excessively toward the pupil area or a center of iris (at 51 in FIG. 21), resulting in a decreased visual acuity of the patient's eyes.

On the other hand, upon such adhesion of the entire circular edge 44E of anterior capsule 36 to the inner surfaces of posterior capsule 38, an annular closed space is defined between the anterior and posterior capsules 36, 38 in a doughnut-like fashion. In the annular closed space, a new natural crystalline lens is gradually formed. The major constituent tissue of the new natural crystalline lens comprises lens fiber cells regenerated in the space. When the natural crystalline lens occupies that closed space, the plural lens fiber cells thereof keep on proliferating and passing through the adhesion area at which the anterior capsule annular edges 44E are adhered to the posterior capsule 38. At last, the lens fiber cells reach a humor chamber outside the posterior capsule 38 and are exposed to aqueous humor in the anterior chamber. Given a certain influence of the aqueous humor, the lens fiber cells become swollen into a plurality of the so-called "Elschnig's pearls", another case of the after-cataract. The Elschnig's pearls scatter a light entering the eye and decrease the visual acuity.

To prevent both foregoing two types of after-cataract, it is important to avoid the adhesion of the anterior capsule edge 44E to the posterior capsule 38. In accordance with the present invention, the intraocular ring assembly 4 works effectively for that purpose. Namely, shortly after completion of the anterior capsulotomy, the ring assembly 4 is inserted through the circular opening (see 44 in FIG. 21) and placed in the inside of the capsular bag 34, whereupon the anterior and posterior capsules 36, 38 are biasingly separated from each other by the respective anterior and posterior ring elements 6, 8, due to the elastic biasing elements 16, thereby keeping the circular opening 44 and its annular edge 44E away from the anterior capsule 36, as understandable from FIG. 21. Thus, there is no such biological adhesion problem stated above between the anterior and posterior capsules 36, 38. Moreover, the fibrous opacification, if any, would occur within a very limited small region around the annular edge 44E and thus will never develop therefrom to the anterior capsule 38. The intraocular ring assembly 4 of the present invention, therefore, insures to prevent the decreased visual acuity due to the fibrous opacification.

In this connection, it is preferable to form grooves and holes in the anterior ring element 6 for the purpose of allowing free circulation of aqueous humor, though not shown. In view of an intimate contact between the anterior ring element 6 and the corresponding area of inner surface of the anterior capsule 36, those grooves and holes will allow a proper amount of the aqueous humor to be flowed between the ring 6 and anterior capsule 36, thereby eliminating a possible increase of transdifferentiated cells and other factors which may produce a great amount of fibrous extracellular matrixes. In that case, therefore, any biological adhesion will not cause between the circular edge 44E and both anterior and posterior capsules 36, 38, and neither will be formed any closed space in the capsular bag 34, the closed space being a place allowing regeneration of lens fibrous cells and incidental formation of Elschnig's pearls therein as mentioned above. Such provision of grooves and holes is a matter of choice to effectively prevent a lowered visual acuity due to the Elschnig's pearls.

Now, reference being made to FIGS. 21 to 23, a specific description will be made of how the artificial lens kit 4 is used for implantation in the capsular bag 34 and how it works for accommodation of the eye therein.

Figure 21:
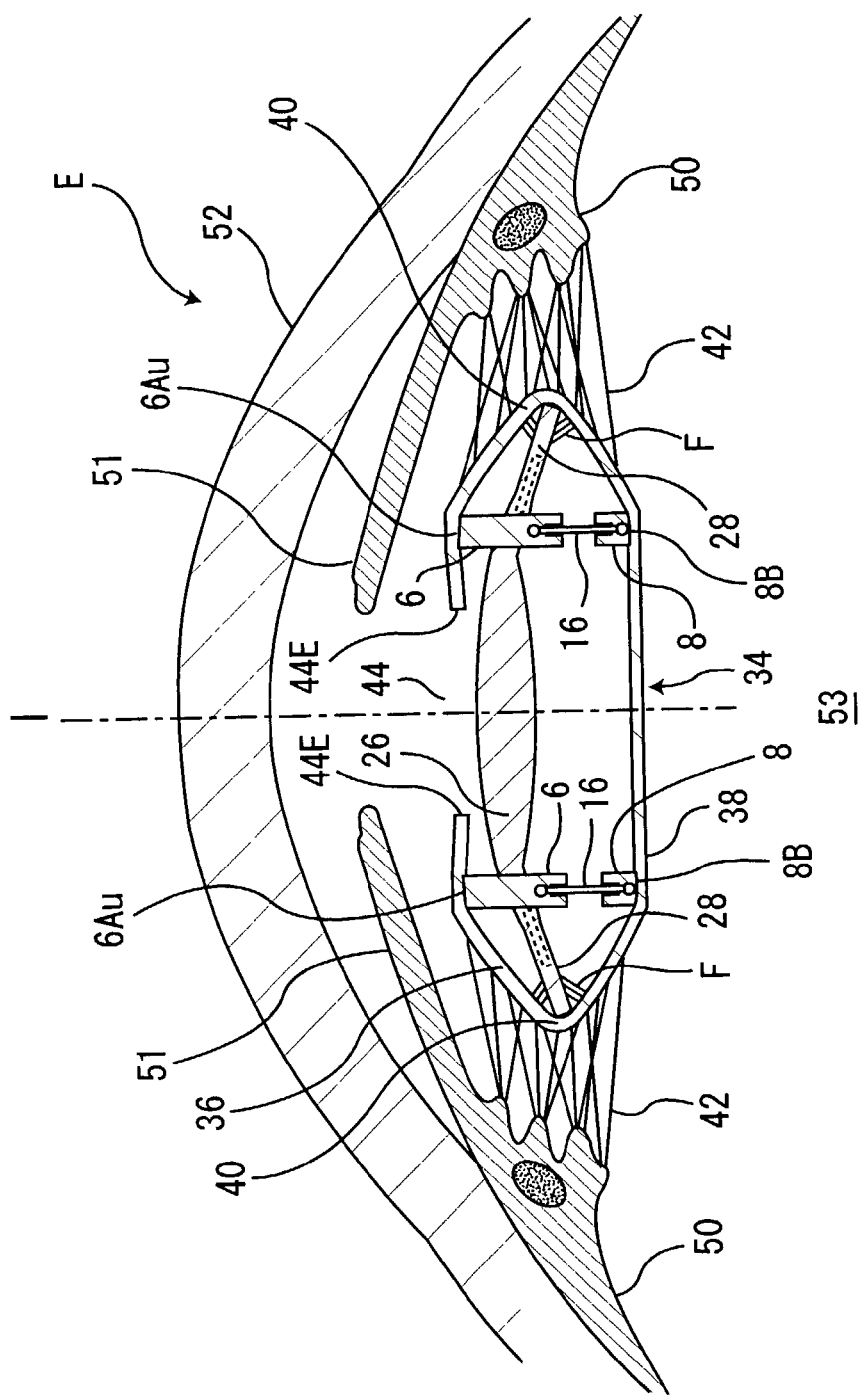
FIG. 21 is a partly broken sectional view showing the state where an assembled unit of the artificial lens kit is implanted in a capsular bag of natural eye.

FIG. 21 depicts the state where the artificial lens kit 4 is used for implantation in a crystalline lens of human eye. In a human eye E, a crystalline lens or a capsular bag 34 is inherently connected at its entire equator region 40 with the zonule 42 which are in turn inherently connected with the circular ciliary muscle 50. Designations 51 and 52 denote a cornea and an iris, respectively. Designation 53 denotes a vitreous body.

At first, an anterior capsulotomy is effected by making a circular incision to the anterior capsule 36 of crystalline lens so as to form a circular opening 44 therein. An inner matrix is then extracted from the crystalline lens via the opening 44 to leave an empty lens capsule or a capsular bag 34. Provided now is one artificial lens kit 2 of the present invention, which is a normally available mode complete with both intraocular ring assembly 34 and intraocular lens 24. First, the intraocular ring assembly 34 is taken from such kit 2 and inserted through the opening 44 into the inside of capsular bag 34. And then, the intraocular lens 24 with a pair of bendable haptic portions 28, taken also from the kit 2, is likewise inserted through the opening 44 into the capsular bag 34 and placed upon the ring assembly 34 therewithin. At this point, a surgeon should rotate the intraocular lens 24 generally coaxially of the ring assembly 34 so that the two haptic portions 28 of the former are respectively dropped and received in a selected diametrically-opposing pair of support recessions 10 of the latter. Thereafter, due to the fibronectin or fibronectin-like substance applied to a part of or a substantially whole of each haptic portion 28 as indicated by Fb or Fb' in FIG. 2, both two haptic portions 28 are firmly and integrally adhered, as indicated at F, to the inner surface regions of capsular bag 34 corresponding to the equator region 40 thereof under the biological adhesive effect induced by the fibronectin or fibronectin-like substance.

In this way, both intraocular lens 24 and ring assembly 4 are assembled and retained in position within the capsular bag 34 in a coaxial relation with each other, wherein their axes extend along the optic axis 1, as can be seen from FIG. 21.

Figure 22:
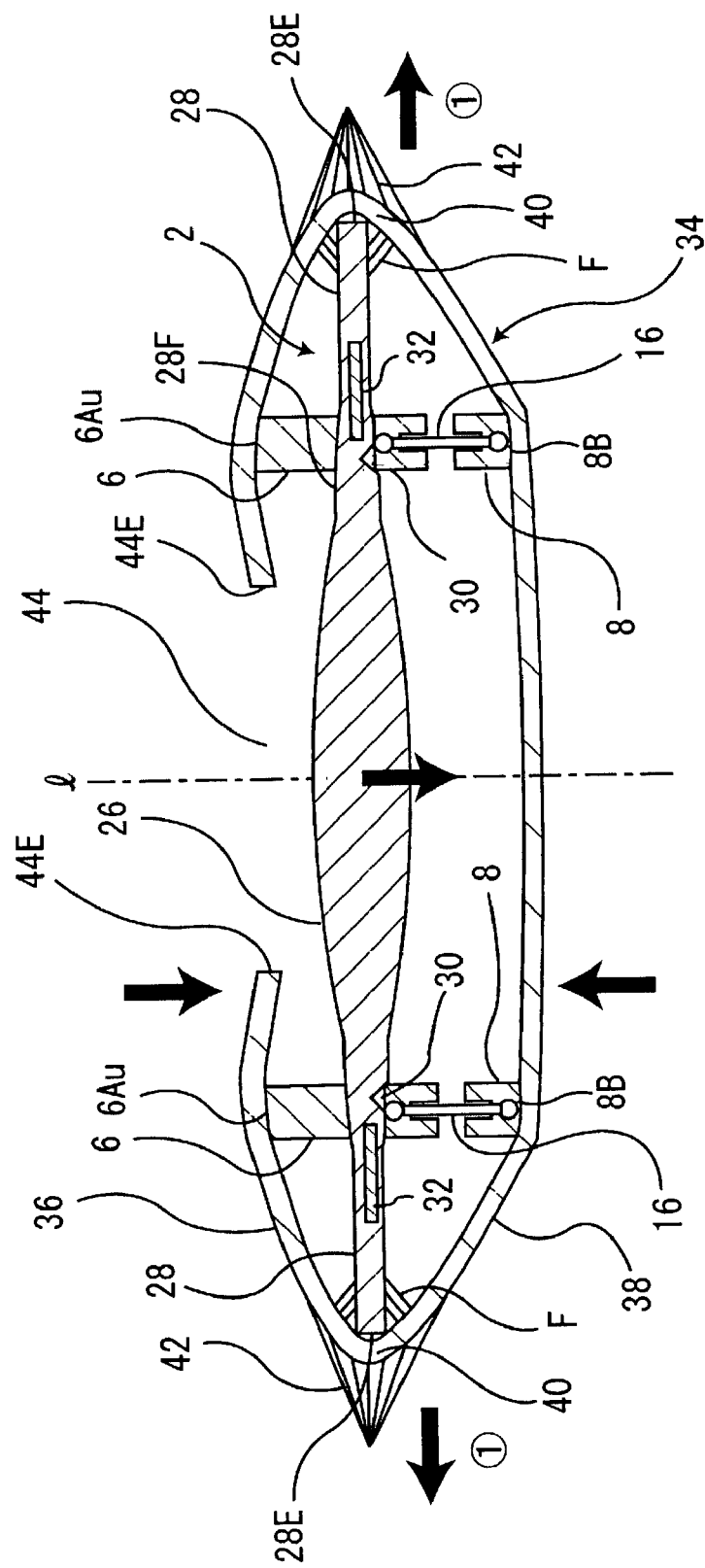
FIG. 22 is a schematic diagram which explanatorily shows the state where the capsular bag becomes flattened via the assembled unit of artificial lens kit when the capsular bag is stretched by traction of ciliary body via the zonule.

Referring now to FIGS. 22 and 23, with the thus-assembled unit of intraocular ring assembly 4 and lens 24 in the capsular bag 34, the anterior ring element 6 is urged by the elastic biasing element 16 into contact with the inner surface of anterior capsule 36, while simultaneously, the posterior ring element 8 is urged by the biasing element 16 into contact with the inner surface of posterior capsule 38. More specifically, the two sloped end faces 6Au, 8B respectively of the posterior and anterior ring elements 6, 8 are biasingly kept in a fit contact with and along the generally concave inner surfaces of posterior and anterior capsules 36, 38. With this structure of ring assembly 4, the capsular bag 34 is retained in a proper biconvex shape while being allowed to be flattened and inflated in a coaxial relation with the optic axis 1, which positively keeps the anterior capsule circular edge 44E away from the posterior capsule 8, as described above. At the same time, both two arcuate ends 28E respectively of the two haptic portions 28 are securely contacted with and along the inner surface regions of capsular bag 34 corresponding to the equator region 40 thereof.

In FIG. 22, upon traction of the capsular bag 34 via the zonule 42 due to relaxation of the ciliary body 50, the capsular bag equator 40 connected with the zonule 42 is drawn outwardly and radially as indicated by the arrows ①, which in turn pulls the haptic portions 28 of lens 24 in diametrically opposite directions. Consequently, as understandable from another arrows, the anterior and posterior capsules 36, 38 are displaced toward each other, whereby the capsular bag 34 is flattened, hence reducing the distance between the anterior and posterior ring elements 6, 8, while resiliently depressing the elastic biasing elements 16, with the result that the two haptic portions 28 received in the support recessions 10 of anterior ring element 6 are extended outwardly and brought to substantially the same line with the equator region 40 (i.e. on substantially rectilinear line) as those two particular haptic portions 28 are articulated relative to their respective two bendable portions 28F or the respective two cutouts 30. Simultaneous therewith, the optic portion 26 is rectilinearly moved along the optic axis 1 in a direction posteriorly of the capsular bag 34 (i.e. toward the posterior capsule 38) and located at a point generally level with the equator 40. Accordingly, the eye E has made a proper accommodation to adjust its focus on a far or distant object.

Conversely, referring to FIG. 23, when the zonule 42 is now relaxed as indicated by ② (due to contraction of the ciliary body 50), the capsular bag 34, which has been stretched outwardly at the equator region 40 thereof as described above, now tends to contract toward its center, reducing the diameter of its equator 40. At this moment, the outwardly biasing force of elastic biasing elements 16 is released from the depressed state so as to urge the anterior and posterior ring elements 6, 8 in a direction away from each other, thereby helping to positively contract the capsular bag 34 into a proper spherical shape. Consequently, as indicated by another arrows, both two haptic portions 28 are bent in one direction toward each other with respect to their respective bendable portions 28F or cutouts 30 and thus displaced nearer to the center of optic portion 26. This simultaneously causes the optic portion 26 to move rectilinearly along the optic axis 1 to a point anteriorly of the capsular bag 34 (i.e. toward the anterior capsule 36). Thus, the eye E has made a proper accommodation to adjust its focus on a near object.

In this connection, preferably, provision of the previously described guide means 22 in the intraocular ring assembly 4 will assist in precise rectilinear movement of the lens 24 along the optical axis 1.

In the foregoing ways, the thus-implanted unit of intraocular lens 24 and ring assembly 4 in the eye E works finely and precisely in response to contraction and relaxation of the zonule 42 as well as to change in shape of whole capsular bag 34, whereby the optic portion 26 is quickly subjected to a proper variation in refractive power and smoothly changes its focus upon a near or distant object being viewed.

It should be understood that the present invention is not limited to the illustrated embodiments, but any other modifications, replacements and additions may be applied thereto without departing from the scopes of the appended claims.

EFFECTS OF THE INVENTION

From the descriptions above, it is appreciated that the intraocular ring assembly 4 and the artificial lens kit 2 in accordance with the present invention has the following effects and advantages:

(1) The intraocular ring assembly 4 in characterized by comprising an anterior ring element 6, a posterior ring element 8, an elastic biasing element 16 securely connected between those two ring elements 6, 8, and support portions 10. The artificial lens kit 2 comprises a novel combination of such intraocular ring assembly 4 and an intraocular lens 24, such that the two bendable haptic portions 28 of intraocular lens 24 is to be movably received in the support portions 10 of the intraocular ring assembly 4, respectively, when implanting an assembled unit of the ring assembly 4 and lens 24 in the lens capsule or capsular bag 34.

(2) The assembled unit of intraocular ring assembly 4 and lens 24 is fitted in substantially a whole inner area of the capsular bag 34 and provides a far increased sensitivity to every change in shape of the capsular bag 34 which is caused by contraction and relaxation of the ciliary body 50 via the zonule 42 adjoining the capsular bag 34, while serving to not only retain an optimum shape of the capsular bag 34, but also preventing after-cataracts as elaborated earlier. Further, the optical portion 26 is precisely moved anteriorly and posteriorly along the optic axis 1 responsive to change in shape of the capsular bag 34. Thus, even after extracapsular cataract extraction, the eye, in which this assembled unit of intraocular ring assembly 4 and lens 24 is implanted, can not only accommodate itself to different distances as naturally and smoothly as a natural crystalline lens does before cataract, but also is prevented from after-cataracts.

(3) In addition, the guide means 22 insures a precise rectilinear movement of both anterior and posterior ring elements 6, 8, which makes positive the rectilinear displacement of the intraocular lens 24 coaxially of the capsular bag 34 along the optic axis 1, thereby realizing an optimum accommodation of the eye (s) without defocusing problem.

What is claimed is:

1. An intraocular ring assembly comprising:
   a first ring element having a center;
   a second ring element having a center;
   at least two recessions defined in said first ring element; and
   a biasing means provided between said first ring element and said second ring element;
   wherein said first and second ring elements are resiliently supported by said biasing means such that the center of said first ring element is in a coaxial relation with the center of said second ring element, and wherein said biasing means resiliently urges said first and second ring elements in a direction opposite to each other;
   wherein said biasing means is integrally and directly connected between said first ring element and said second ring element; and
   wherein said biasing means comprises at least two elastic elements, each being of a generally "O" shape having one end portion integrally and continuously connected with said first ring element and another end portion integrally and continuously connected with said second ring element.

2. An intraocular ring assembly comprising:
   a first ring element having a center;
   a second ring element having a center;
   at least two recessions defined in said first ring element; and
   a biasing means provided between said first ring element and said second ring element;
   wherein said first and second ring elements are resiliently supported by said biasing means such that the center of said first ring element is in a coaxial relation with the center of said second ring element, and wherein said biasing means resiliently urges said first and second ring elements in a direction opposite to each other;
   which further comprises a guide means provided between said first and second ring elements, said guide means being adapted to assist in a rectilinear coaxial movement of the first and second ring elements; and;
   wherein said guide means comprises at least one cylindrical guide member provided in one of said first and second ring elements and at least one guide rod slidably inserted in said cylindrical guide member, said at least one guide rod being provided in another of said first and second ring elements.

3. An artificial lens kit for implantation in a lens capsule of natural eye in which the lens capsule has an equator, comprising:
   an intraocular lens having an optic portion and a haptic means provided on a peripheral end of said optic portion; said haptic means being adapted to contact an inner surface region of said lens capsule corresponding to said equator; and
   an intraocular ring assembly in which said intraocular lens is supported in a coaxial relation therewith, said intraocular ring assembly including:
   a first ring element having a center and a support means for supporting said haptic means of said intraocular lens therein;
   a second ring element having a center;
   a biasing means provided between said first ring element and said second ring element, wherein said first and second ring elements are resiliently urged by said biasing means in a direction opposite to each other, such that the center of said first ring element is in a coaxial relation with the center of said second ring element;
   wherein said haptic means comprises at least two haptic portions each including a bendable means defined adjacent to a base area thereof, said bendable means being adapted to render each of said at least two haptic portions bendable at said base area in a vertical direction with respect to said optic portion; and
   wherein said bendable means comprises a cutout formed in one side of each of said at least two haptic portions in proximity to said base area.

4. An artificial lens kit for implantation in a lens capsule of natural eye in which the lens capsule has an equator, comprising:
   an intraocular lens having an optic portion and a haptic means provided on a peripheral end of said optic portion; said haptic means being adapted to contact an inner surface region of said lens capsule corresponding to said equator; and
   an intraocular ring assembly in which said intraocular lens is supported in a coaxial relation therewith, said intraocular ring assembly including:
   a first ring element having a center and a support means for supporting said haptic means of said intraocular lens therein;
   a second ring element having a center;
   a biasing means provided between said first ring element and said second ring element, wherein said first and second ring elements are resiliently urged by said biasing means in a direction opposite to each other, such that the center of said first ring element is in a coaxial relation with the center of said second ring element;

wherein said biasing means is integrally and directly connected between said first ring element and said second ring element; and wherein said biasing means comprises at least two elastic elements, each being of a generally "O" shape having one end portion integrally and continuously connected with said first ring element and an end portion integrally and continuously connected with said second ring element.

5. An artificial lens kit for implantation in a lens capsule of natural eye in which the lens capsule has an equator, comprising:

an intraocular lens having an optic portion and a haptic means provided on a peripheral end of said optic portion; said haptic means being adapted to contact an inner surface region of said lens capsule corresponding to said equator; and an intraocular ring assembly in which said intraocular lens is supported in a coaxial relation therewith, said intraocular ring assembly including:

a first ring element having a center and a support means for supporting said haptic means of said intraocular lens therein;

a second ring element having a center;

a biasing means provided between said first ring element and said second ring element, wherein said first and second ring elements are resiliently urged by said biasing means in a direction opposite to each other, such that the center of said first ring element is in a coaxial relation with the center of said second ring element;

which further comprises a guide means provided between said first and second ring elements, said guide means being adapted to assist in a rectilinear coaxial movement of the first and second ring elements; and wherein said guide means comprises a cylindrical guide member provided in one of said first and second ring elements and a guide rod slidably inserted in said cylindrical guide member, said guide rod being provided in another of said first and second ring elements.

* * * * *